US011547665B2

(12) United States Patent
Garraway et al.

(10) Patent No.: US 11,547,665 B2
(45) Date of Patent: Jan. 10, 2023

(54) MULTIPHASIC COMPOSITIONS

(71) Applicant: SEQUESSOME TECHNOLOGY HOLDINGS LIMITED, Valletta (MT)

(72) Inventors: Richard Wolf Garraway, Greater London (GB); William Henry, Greater London (GB)

(73) Assignee: SEQUESSOME TECHNOLOGY HOLDINGS LIMITED, Valletta (MT)

( * ) Notice: Subject to any disclaimer, the term of this patent is extended or adjusted under 35 U.S.C. 154(b) by 73 days.

(21) Appl. No.: 16/929,009

(22) Filed: Jul. 14, 2020

(65) Prior Publication Data

US 2021/0007989 A1  Jan. 14, 2021

Related U.S. Application Data

(63) Continuation of application No. 15/739,575, filed as application No. PCT/EP2016/065425 on Jun. 30, 2016, now Pat. No. 10,744,090.

(30) Foreign Application Priority Data

Jun. 30, 2015 (GB) ..................................... 1511469
Jun. 30, 2015 (GB) ..................................... 1511478

(51) Int. Cl.
*A61K 9/127* (2006.01)
*A61K 47/24* (2006.01)
*A61K 47/26* (2006.01)
*A61K 31/155* (2006.01)
*A61K 31/165* (2006.01)
*A61K 31/355* (2006.01)
*A61K 31/522* (2006.01)
*A61K 31/60* (2006.01)
*A61K 31/618* (2006.01)
*A61Q 19/08* (2006.01)
*A61K 9/10* (2006.01)
*A61K 31/7008* (2006.01)
*A61K 31/737* (2006.01)
*A61K 8/04* (2006.01)
*A61Q 19/00* (2006.01)
*A61Q 19/02* (2006.01)
*A61K 9/00* (2006.01)
*A61P 17/10* (2006.01)
*A61P 17/04* (2006.01)
*A61K 8/14* (2006.01)
*A61K 33/30* (2006.01)

(52) U.S. Cl.
CPC .............. *A61K 9/1272* (2013.01); *A61K 8/04* (2013.01); *A61K 8/14* (2013.01); *A61K 9/0014* (2013.01); *A61K 9/10* (2013.01); *A61K 9/127* (2013.01); *A61K 31/155* (2013.01); *A61K 31/165* (2013.01); *A61K 31/355* (2013.01); *A61K 31/522* (2013.01); *A61K 31/60* (2013.01); *A61K 31/618* (2013.01); *A61K 31/7008* (2013.01); *A61K 31/737* (2013.01); *A61K 47/24* (2013.01); *A61K 47/26* (2013.01); *A61P 17/04* (2018.01); *A61P 17/10* (2018.01); *A61Q 19/00* (2013.01); *A61Q 19/02* (2013.01); *A61Q 19/08* (2013.01); *A61K 33/30* (2013.01); *A61K 2300/00* (2013.01)

(58) Field of Classification Search
None
See application file for complete search history.

(56) References Cited

U.S. PATENT DOCUMENTS

| | | |
|---|---|---|
| 4,372,296 A | 2/1983 | Fahim |
| 5,015,483 A | 5/1991 | Haynes et al. |
| 5,498,420 A | 3/1996 | Edgar et al. |
| 5,498,607 A | 3/1996 | Hsia et al. |
| 5,614,215 A | 3/1997 | Ribier et al. |
| 5,853,753 A | 12/1998 | Maierhofer et al. |
| 6,165,500 A | 12/2000 | Cevc |
| 6,191,121 B1 | 2/2001 | Cone |
| 6,248,728 B1 | 6/2001 | Koo |
| 6,534,070 B1 | 3/2003 | Franke et al. |
| 7,175,850 B2 | 2/2007 | Cevc |
| 7,476,432 B2 | 1/2009 | Pringle et al. |
| 7,544,375 B1 | 6/2009 | Bellin et al. |

(Continued)

FOREIGN PATENT DOCUMENTS

| | | |
|---|---|---|
| CN | 1826123 A | 8/2006 |
| EA | 200800441 A1 | 8/2008 |

(Continued)

OTHER PUBLICATIONS

Allison, K., "Taking the Pain out of Runner's Knee," Harvard Health Blog—Harvard Health Publishing, Sep. 29, 2011, one page. [Online] Retrieved from the internet on Dec. 10, 2018, Retrieved from <URL: https://www.health.harvard.edu/blog/taking-the-pain-out-of-runners-knee-201106072801>.

(Continued)

*Primary Examiner* — Nannette Holloman
(74) *Attorney, Agent, or Firm* — Wilmer Cutler Pickering Hale and Dorr LLP

(57) ABSTRACT

The present invention relates to compositions comprising a colloidal dispersion and an Agent of Interest ("AOI"), wherein the colloidal dispersion comprises deformable colloidal particles and wherein the AOI is not associated with the deformable colloidal particles. The present invention also provides kits and transdermal drug release devices comprising the compositions of the present invention, and the use of these compositions in medicine, skin care and cosmetics.

8 Claims, 5 Drawing Sheets

(56) References Cited

U.S. PATENT DOCUMENTS

| | | | |
|---|---|---|---|
| 7,867,480 | B1 | 1/2011 | Cevc et al. |
| 8,367,100 | B2 * | 2/2013 | Smith ..................... A61P 23/02 604/290 |
| 9,452,179 | B2 | 9/2016 | Kroon et al. |
| 9,555,051 | B2 | 1/2017 | Mayo et al. |
| 2002/0012680 | A1 | 1/2002 | Patel et al. |
| 2003/0064948 | A1 | 4/2003 | Fahr et al. |
| 2003/0099694 | A1 | 5/2003 | Cevc et al. |
| 2003/0161867 | A1 | 8/2003 | Lu et al. |
| 2004/0071767 | A1 | 4/2004 | Cevc et al. |
| 2004/0105881 | A1 | 6/2004 | Cevc et al. |
| 2005/0123593 | A1 | 6/2005 | Thompson et al. |
| 2007/0042008 | A1 | 2/2007 | Kane et al. |
| 2007/0224256 | A1 | 9/2007 | Bolton et al. |
| 2007/0238708 | A1 | 10/2007 | Mandel et al. |
| 2008/0095722 | A1 | 4/2008 | Cevc et al. |
| 2008/0268042 | A1 | 10/2008 | Feuerstein et al. |
| 2009/0060990 | A1 | 3/2009 | Cevc et al. |
| 2009/0324727 | A1 | 12/2009 | Roca |
| 2010/0098749 | A1 | 4/2010 | Barenholz et al. |
| 2010/0105139 | A1 | 4/2010 | Spanjaard |
| 2010/0130611 | A1 | 5/2010 | Feuerstein et al. |
| 2010/0197621 | A1 | 8/2010 | Henry et al. |
| 2012/0045405 | A1 | 2/2012 | Gilman et al. |
| 2012/0220669 | A1 | 8/2012 | Mayo et al. |
| 2012/0232034 | A1 | 9/2012 | Kroon et al. |
| 2012/0294924 | A1 | 11/2012 | Tice et al. |
| 2014/0100191 | A1 | 4/2014 | Kroon et al. |
| 2015/0057249 | A1 | 2/2015 | Mayo et al. |
| 2015/0065461 | A1 | 3/2015 | Garraway et al. |
| 2015/0125407 | A1 | 5/2015 | Henry et al. |
| 2015/0132349 | A1 | 5/2015 | Garraway et al. |
| 2016/0175448 | A1 | 6/2016 | Mayo et al. |
| 2016/0193147 | A1 | 7/2016 | Garraway et al. |
| 2018/0311148 | A1 | 11/2018 | Garraway et al. |

FOREIGN PATENT DOCUMENTS

| | | |
|---|---|---|
| EP | 0220797 A2 | 5/1987 |
| EP | 0475160 A1 | 3/1992 |
| EP | 1551370 B1 | 4/2004 |
| EP | 2382994 A1 | 11/2011 |
| ES | 2107668 T3 | 12/1997 |
| JP | 4-55167 B2 | 9/1992 |
| JP | 7-206879 A | 8/1995 |
| JP | 8-509202 A | 10/1996 |
| JP | 11-139956 A | 5/1999 |
| JP | 11-507369 A | 6/1999 |
| JP | 2001-523723 A | 11/2001 |
| JP | 2004-131432 A | 4/2004 |
| JP | 2005-515242 A | 5/2005 |
| JP | 2005-179313 A | 7/2005 |
| JP | 2006-525368 A | 11/2006 |
| JP | 2006-528136 A | 12/2006 |
| JP | 2007-269720 A | 10/2007 |
| JP | 2008-127327 A | 6/2008 |
| JP | 2009-506120 A | 2/2009 |
| JP | 2009-256331 A | 11/2009 |
| NZ | 332905 | 12/2000 |
| NZ | 296098 | 5/2001 |
| WO | WO-1987/001938 A1 | 4/1987 |
| WO | WO-1998/017255 A1 | 4/1998 |
| WO | WO-1999/022703 A1 | 5/1999 |
| WO | WO-1999/036053 A1 | 7/1999 |
| WO | WO-2000/012060 A1 | 3/2000 |
| WO | WO-2000/045774 A1 | 8/2000 |
| WO | WO-2001/076555 A2 | 10/2001 |
| WO | WO-2003/077861 A2 | 9/2003 |
| WO | WO-2004/006954 A2 | 1/2004 |
| WO | WO-2005/007169 A2 | 1/2005 |
| WO | WO-2006/086992 A2 | 8/2006 |
| WO | WO-2008/039989 A2 | 4/2008 |
| WO | WO-2008/077641 A1 | 7/2008 |
| WO | WO-2008/156646 A1 | 12/2008 |
| WO | WO-2009/093193 A2 | 6/2009 |
| WO | WO-2009/106338 A2 | 9/2009 |
| WO | WO-2010/140061 A2 | 12/2010 |
| WO | WO-2011/022707 A1 | 2/2011 |
| WO | WO-2011/162802 A1 | 12/2011 |
| WO | WO-2013/144289 A1 | 10/2013 |
| WO | WO-2013/153221 A1 | 10/2013 |
| WO | WO-2013/171131 A1 | 11/2013 |
| WO | WO-2013/171132 A1 | 11/2013 |
| WO | WO-2015/014965 A1 | 2/2015 |

OTHER PUBLICATIONS

Collins, J., et al., "Flexiseq® Sport (TOT 064): A Drug-Free Alternative for the Treatment of Joint Pain and Muscle Soreness Following Exercise—Avoiding the Risks of Commonly Used Drug Therapies such as NSAIDS," Presented at the International Sports Science and Sports Medicine Conference, Sep. 8-10, 2015, Newcastle upon Tyne, UK, 5 pages.

webmd.com, "Osteoarthritis: Symptoms & Types," Date Unknown, five pages. [Online] Retrieved from the Internet on Mar. 6, 2018, Retrieved from <URL: http://www.webmd.com/osteoarthritis/guide/osteoarthritis-symptoms-types>.

webmd.com, "Runner's Knee: Pain and Treatment," 2010, two pages. [Online] Retrieved from the Way Back Machine from Dec. 19, 2010, Retrieved from <URL: http://web.archive.org/web/20101219060759/www.webmd.com/pain-management/knee-pain/runners-knee>.

PCT International Search Report and Written Opinion for PCT/US2010/046245, dated Oct. 1, 2010, 29 Pages.

PCT International Preliminary Report on Patentability for PCT/US2010/046245, dated Oct. 24, 2011, 30 Pages.

PCT International Search Report and Written Opinion for PCT/EP2013/056694, dated Jun. 21, 2013, 8 Pages.

PCT International Search Report and Written Opinion for PCT/IB2010/001557, dated Jun. 6, 2011, 12 Pages.

PCT International Search Report and Written Opinion for PCT/EP2013/057742, dated May 21, 2013, 11 Pages.

PCT International Search Report and Written Opinion for PCT/EP2013/059741, dated Jul. 23, 2013, 9 Pages.

PCT International Search Report and Written Opinion for PCT/EP2013/059740, dated Sep. 20, 2013, 19 Pages.

PCT International Search Report and Written Opinion for PCT/EP2014/066545, dated Oct. 15, 2014, 15 Pages.

PCT International Search Report and Written Opinion for PCT/EP2016/065425, dated Sep. 12, 2016, 14 Pages.

PCT International Search Report and Written Opinion for PCT/EP2016/065415, dated Sep. 12, 2016, 14 Pages.

Search Report for Great Britain Patent Application No. GB1511478.8, dated Mar. 18, 2016, 5 Pages.

Search Report for Great Britain Patent Application No. GB1511469.7, dated Mar. 18, 2016, 5 Pages.

Barthel, H. R., et al., "Randomized Controlled Trial of Diclofenac Sodium Gel in Knee Osteoarthritis," Semin Arthritis Rheum., 2009, pp. 203-212, vol. 39, No. 3.

Bayer: Bepanthen-Spray Mousse Rafraichissant (patient information leaflet), Dec. 10, 2007, XP002636839.

Conaghan, P. G., et al., "FRI0300 A large randomised, controlled trial comparing the efficacy and safety of topical ketoprofen in transfersome gel with oral celecoxib for osteoarthritis knee pain," Annals of the Rheumatic Diseases, 2013, p. 415, 71 (Suppl 3).

Cevc, G., "Transfersomes, Liposomes and Other Lipid Suspensions on the Skin: Permeation Enhancement, Vesicle Penetration, and Transdermal Drug Delivery," Critical Reviews in Therapeutic Drug Carrier Systems, 1996, pp. 257-388, vol. 13, Nos. 3 and 4.

Cevc, G., et al., "Ultraflexible vesicles, Transfersomes, have an extremely low pore penetration resistance and transport therapeutic amounts of insulin across the intact mammalian skin," Biochemica et Biophysica Acta, 1998, pp. 201-215, vol. 1368.

Cevc, G., et al., "Ultradeformable lipid vesicles can penetrate the skin and other semi-permeable barriers unfragmented. Evidence

(56) References Cited

OTHER PUBLICATIONS from double label CLSM experiments and direct size measurements," Biochimica et Biophysica Acta, 2002, pp. 21-30.
Crosasso, P., et al., "Preparation, characterization and properties of sterically stabilized paclitaxel-containing liposomes," Journal of Controlled Release, 2000, pp. 19-30.
Dieppe, P. et al., "Pathogenesis and management of pain in osteoarthritis," The Lancet, 2005, pp. 965-973, vol. 365.
Gallarate, M., et al., "Deformable Liposomes as Topical Formulations Containing α-Tocopherol," Journal of Dispersion Science and Technology, 2006, pp. 703-713, vol. 27, No. 5.
Gong, Y-K., et al., "Strategies in biomimetic surface engineering of nanoparticles for biomedial applications," Nanoscale, Oct. 20, 2011, pp. 360-368, vol. 4.
Idea Ag, "Updates on Diractin® (ketoprofen in Transfersome® gel) status," Oct. 7, 2009, Munich, Germany, [online] [Retrieved on Aug. 17, 2016] Retrieved from the Internet <URL:http://www.technostart.com/down/r_d_2_091007_PR_Diractin.pdf>.
Idea Ag, "Multicenter, Randomized, Double-Blind, Placebo- and Active-Controlled Study of Safety and Efficacy of Two Dosages of Epicutaneously Applied Diractin® (Ketoprofen in Transfersome® Gel) for the Treatment of Osteoarthritis of the Knee," Jan. 1, 2009, [online][Retrieved on Apr. 26, 2016] Retrieved from the Internet <URL:https://clinicaltrials.gov/archive/NCT00716547/2009_01_20>.
Janiczek-Dolphin, N., et al., "Can sebum reduction predict acne outcome?" British Journal of Dermatology, May 28, 2010, vol. 163, Issue 4, pp. 683-688.
Kamatou, G.P.P., et al., "South African *salvia* species: A review of biological activities and phytochemistry," Journal of Ethnopharmacology, 2008, pp. 664-672, vol. 119.
Kawano, T., et al., "Mechanical Effects of the Intraarticular Administration of High Molecular Weight Hyaluronic Acid Plus Phospholipid on Synovial Joint Lubrication and Prevention of Articular Cartilage Degeneration in Experimental Osteoarthritis," Arthritis & Rheumatism, 2003, pp. 1923-1929, vol. 48, No. 7.
KLOX Technologies Inc., "KLOX Technologies Announces Approval in Canada of its Innovative Acne Vulgaris Treatment," Oct. 2, 2013, 2 Pages, Retreived from <URL:https:lwww.newswire.ca/news-releases/klox-technologies-announces-approval-in-canada-of-its-innovative-acne-vulgaris-treatment-513043711.html>.
Knee Joint Picture [online][Retrieved on May 4, 2016] Retrieved from the Internet <URL: http://www.medicinenet.com/image-collection/knee%20_joint_picture/picture.htm>.
Kneer, W., et al., "A Multiple-Dose, Open-Label, Safety, Compliance, and Usage Evaluation Study of Epicutaneously Applied Diractin® (Ketoprofen in Transfersome®) in Joint/Musculoskeletal Pain or Soft Tissue Inflammation," Current Drug Safety, 2009, pp. 5-10, vol. 4.
Lahey Hospital & Medical Center, "Lecithin," 2016, 6 Pages.
Mezei, M., et al., "Dermatitic Effect of Nonionic Surfactants IV: Phospholipid Composition of Normal and Surfactant-Treated Rabbit Skin," Journal of Pharmaceutical Sciences, 1970, pp. 858-861, vol. 59, No. 6.
Osteoarthritis Symptoms and Causes [online][Retrieved on May 4, 2016] Retrieved from the Internet <URL:http://www.mayoclinic.org/diseases-conditions/osteoarthritis/symptoms-causes/dxc-20198250>.
Roth, S. H., et al., "Efficacy and Safety of a Topical Diclofenac Solution (Pennsaid) in the Treatment of Primary Osteoarthritis of the Knee," Arch Intern Med., 2004, pp. 2017-2023, vol. 164, No. 18.
Rother, M., et al., "Efficacy and safety of epicutaneous ketoprofen in Transfersome (IDEA-033) versus oral celecoxib and placebo in osteoarthritis of the knee: multicentre randomised controlled trial," Annals of the Rheumatic Diseases, 2007, pp. 1178-1183, vol. 66.
Sivan, S., et al., "Liposomes Act as Effective Biolubricants for Friction Reduction in Human Synovial Joints," Langmuir, 2010, pp. 1107-1116, vol. 26, No. 2.
Simoes, S. I., et al., Permeabilisation and solubilisation of soybean phosphatidylcholine bilayer vesicles, as membrane models, by polysorbate, Tween 80, European Journal of Pharmaceutical Sciences, 2005, pp. 307-317, vol. 26.
Skalko, N., et al., "Liposomes with Metronidazole for Topical Use: The Choice of Preparation Method and Vehicle," Journal of Liposome Research, 1998, pp. 283-293, vol. 8, No. 2.
Sumida, Y., "Application of a Liposome Technique to Cosmetics," Membrane, 1998, pp. 144-152, vol. 24, No. 3. (English abstract).
Sundaram, H., "Cosmetics Challenge: Six Stratetgies for Scientific Skincare, Part 2 of 2," Practical Dermatology, Aug. 2010, 3 Pages, Retrieved at <URL:http://practicaldermatology.com/2010/08/cosmetics-challenge-six-strateg ies-for-scientific-skincare-part-2-of-2>.
Tavano, L., et al., "Niosomesmicroemulsions: New carriers for topical delivery of Capsaicin", Colloids and Surfaces. B, Biointerfaces, Elsevier, Amsterdam, NL, vol. 87, No. 2, May 20, 2011, pp. 333-339.
Treede, I., et al., "Anti-Inflammatory Effects of Phosphatidylcholine," The Journal of Biological Chemistry, 2007, pp. 27155-27164, vol. 282, No. 37.
Trif, M., et al., "Liposomes-entrapped chondroitin sulphate: Ultrastructural characterization and in vitro biocompatibility",Micron, Pergamon, Oxford, GB, vol. 39, No. 7, Oct. 1, 2008, pp. 1042-1045.
Withdrawal Assessment Report for Diractin; EMEA—European Medicines Agency, Oct. 23, 2008, London, UK, 24 Pages.
Kang, M.J. et al., "Folic acid-tethered Pep-I peptide-conjugated liposomal nanocarrier for enchanced intracellular drug delivery to cancer cells: conformational characterization and invitro cellular uptake evaluation", International Journal of Nanomedicine, 2013, vol. 8: pp. 1155-1165.
Pitman, S., "Tripeptide features as key ingredient in anti-aging launches", Retrieved from the internet: https://www.cosmeticsesign.com/Article/2007/0416/Tripeptide-features-as-key-ingredient-in-anti-aging-launches.
Mayo Clinic, "Carpal Tunnel Syndrome—Symptoms and Causes," Date Unknown, six pages. [Online] Retrieved from the Internet on Mar. 8, 2018, Retrieved from <URL: https://www.mayoclinic.org/diseases-conditions/carpal-tuneel-syndrome/symptoms-causes/syc-20355603>.
PCT International Preliminary Report on Patentability, International Application No. PCT/EP2016/065425, dated Jan. 11, 2018, 10 pages.
United States Office Action, U.S. Appl. No. 14/055,269, dated Jul. 1, 2015.
United States Office Action, U.S. Appl. No. 14/388,469, dated Mar. 8, 2016.
United States Office Action, U.S. Appl. No. 14/908,494, dated Nov. 18, 2019.
United States Office Action, U.S. Appl. No. 14/908,494, dated Mar. 7, 2019.
United States Office Action, U.S. Appl. No. 14/908,494, dated May 31, 2018.
United States Office Action, U.S. Appl. No. 14/908,494, dated Jan. 30, 2018.
United States Office Action, U.S. Appl. No. 15/349,792, dated Oct. 10, 2019.
United States Office Action, U.S. Appl. No. 15/349,792, dated Mar. 14, 2018.
United States Office Action, U.S. Appl. No. 15/349,792, dated Aug. 18, 2017.
United States Office Action, U.S. Appl. No. 15/739,570, dated Sep. 27, 2019.
United States Office Action, U.S. Appl. No. 15/739,570, dated Mar. 28, 2019.
Kosai et al., "Effect of Capsaicin Cream on Neuropathic Pain," Journal of Japan Society of Pain Clinicians, Jan. 25, 1999, vol. 6(1), pp. 26-30. English Abstract, 3 pages.
Mandom Corp. News Release, "Elucidation of analgesia mechanism by Mandom and menthol," Dec. 10, 2015, English translation, 6 pages. (URL:https://www.mandom.co.jp/release/pdf/2015121001.pdf).

\* cited by examiner

MULTIPHASIC COMPOSITIONS

RELATED APPLICATIONS

This application is a continuation of U.S. application Ser. No. 15/739,575, allowed, which is the National Stage of International Application No. PCT/EP2016/065425 filed Jun. 30, 2016, which claims priority to GB application no. 1511469.7, filed Jun. 30, 2015, and GB application no. 1511478.8, filed Jun. 15, 2015, each of which is herein incorporated in its entirety by reference

SUMMARY OF THE INVENTION

The present invention relates to compositions comprising a colloidal dispersion and an Agent of Interest ("AOI"), wherein the colloidal dispersion comprises deformable colloidal particles and wherein the AOI is not associated with the deformable colloidal particles. The present invention also provides kits and transdermal drug release devices comprising the compositions of the present invention, and the use of these compositions in medicine, skin care and cosmetics.

BACKGROUND

Colloidal dispersions containing colloidal particles comprising a non-ionic surfactant and a phospholipid which are free of any AOI are known from WO 2010/140061. WO 2010/140061 describes the use of such drug-free ("empty") colloidal dispersions for the treatment of deep tissue pain, specifically pain associated with osteoarthritis. In WO 2011/022707, drug-free colloidal dispersions are used for treating atopic eczema, dishydrotic hand eczema, plaque type psoriasis, seborrheic eczema and acne vulgaris.

Colloidal particles have also been used to deliver AOIs through the skin. For example, WO 2015/014965 discloses colloidal dispersions that contain colloidal particles comprising a non-ionic surfactant and a phospholipid, wherein the colloidal dispersions comprise an AOI. WO 2015/014965 describes the use of these colloidal dispersions for the topical administration of a therapeutic, metabolic or structural AOI that is "tethered" to the lipid and/or the surfactant component of the colloidal particle. For example, colloidal dispersions comprising anti-oxidants or vitamins are used for enhancing the skin's ability to repair, and colloidal dispersions comprising vitamin D may be used to supplement sun cream in order to prevent vitamin D deficiency.

In some instances, such as in WO 2013/171131, an active agent is applied directly to the skin and a drug-free colloidal dispersion is applied over the active agent to simply "push" it through the skin.

None of these documents disclose or teach a single composition comprising a colloidal dispersion and an AOI, wherein the colloidal dispersion comprises deformable colloidal particles and wherein the AOI is not associated with the deformable colloidal particles.

Citation of any reference in this section of the application is not an admission that the reference is prior art to the invention. The above noted publications are hereby incorporated by reference in their entirety.

Providing an AOI inside a colloidal particle such as a vesicle can prevent the active agent from contacting the appropriate receptors within the body, and thus reduce the efficacy of the composition. Bonding an active agent to an external surface of a colloidal particle can result in the active agent penetrating past the desired target tissues of the subject when applied topically. Applying an AOI directly to the skin, followed by a drug-free colloidal dispersion, means that there is little or no dose control of the application of the AOI. An indeterminate amount of AOI is applied to the skin followed by an indeterminate amount of colloidal dispersion. It is impossible for the user to be certain about how much AOI is being delivered through the skin. In addition, the application of an AOI directly to the skin means that it is applied at a high concentration and is more likely to cause adverse skin reactions. Furthermore, having to individually apply two or more compositions is particularly time consuming for the user as each composition may take up to 10 minutes to dry.

DETAILED DESCRIPTION

The current invention circumvents these problems by combining the AOI with deformable colloidal particles in a single easy-to-apply composition, wherein the AOI is not associated with the deformable colloidal particles. The inventors have surprisingly found that such compositions are stable and that they increase the absorption of the AOI into the skin of an animal whilst preventing the AOI from penetrating too deeply. Even when not associated with the AOI, the deformable colloidal particles have been found to drive the AOI through the skin to increase speed, depth and effectiveness of absorption. Furthermore, the provision of both the AOI and the deformable colloidal particles in a single composition means that both components can be administered together in one easy application. This saves time for the user, reduces adverse skin reactions and ensures more accurate dosing (on a gram-for-gram basis there is a consistent ratio of the AOI to the deformable colloidal particles).

Accordingly, the first aspect of the invention comprises a composition comprising a colloidal dispersion and an AOI, wherein said colloidal dispersion comprises deformable colloidal particles comprising a surfactant and optionally a phospholipid and wherein the AOI is not associated with the deformable colloidal particles.

As used herein, the phrase "not associated with" means that the AOI is not attached to or contained within the deformable colloidal particle. In particular, the AOI is not tethered, bound or otherwise secured to the deformable colloidal particle, is not contained within the structure of the deformable colloidal particle, including the lipid bilayer or the fluid enclosed by the lipid bilayer, is not encapsulated within the deformable colloidal particle or in any other way directly associated with the deformable colloidal particle. Rather, the AOI is present in a different phase of the composition from the deformable colloidal particles. For example, the AOI may be present within the continuous phase of the composition, for example dissolved in the continuous phase. Alternatively, the AOI may be present within a different dispersed phase of the composition, for example in the form of insoluble aggregates or associated with non-deformable colloidal particles such as micelles and non-deformable vesicles such as liposomes. Preferably, the AOI is in a form in which it would not normally pass through the skin, without the assistance of deformable colloidal particles.

The composition of the present invention is multiphasic as it comprises at least two phases; a dispersed phase comprising the suspended deformable colloidal particles and a continuous phase comprising the medium of suspension. In a multiphasic system there are discrete particles, assemblies or bodies dispersed or suspended within a medium or matrix. Each phase is a separate solid or liquid entity with a detectable phase boundary. In colloidal systems, the particle size of each phase is too small for observation with the naked eye. However, the multiphasic nature of the system can be demonstrated by applying a narrow beam of light, a Tyndall Beam, the passage of which is visible through the solution due to scattering of the light by the phase boundary(ies). The passage of such a beam of light through a single phase solution would not be visible.

The composition of the present invention may be a biphasic composition, comprising a single dispersed phase and a single continuous phase. In such embodiments, the AOI may be dissolved in the continuous phase.

Alternatively, the composition of the present invention may comprise more than two phases. For example, the composition may comprise two, three, four or more dispersed phases, in addition to the continuous phase. One such dispersed phase will comprise the deformable colloidal particles which drive the AOI through the skin. A second dispersed phase may comprise the AOI, for example in the form of insoluble aggregates or associated with non-deformable colloidal particles. Other dispersed phases may also be provided comprising further deformable and/or non-deformable colloidal particles.

The composition may comprise one or more colloidal dispersions.

Preferably, the continuous phase comprises a non-lipid phase. The continuous phase may be selected depending upon the identity of the AOI and whether the AOI is to be dissolved in the continuous phase or provided as a dispersed phase. Preferably, the continuous phase is an aqueous phase.

Whilst all of the AOI may be provided in a separate phase from the deformable colloidal particles, under certain circumstances, which will be well known to those of skill in the art, some of the AOI may partition into the membrane or the fluid core of the deformable colloidal particles. Preferably, only a negligible or insignificant amount of the AOI provided in a separate phase from the deformable colloidal particles partitions into the deformable colloidal particles, whilst a significant amount of the AOI remains in a separate phase. Preferably, about 5% or less, about 4% or less, about 3% or less, about 2% or less, about 1% or less, about 0.5% or less, about 0.1% or less or about 0% of the AOI partitions into the deformable colloidal particles. Preferably, at least about 95.0%, at least about 96.0%, at least about 97.0%, at least about 98.0%, at least about 99.0%, at least about 99.5%, at least about 99.9% or about 100% of the AOI in the composition remains in a separate phase from the deformable colloidal particles.

Alternatively, the composition according to the first aspect of the present invention may comprise two significant populations of the same AOI; a first population that is not associated with the deformable colloidal particles and a second population that is associated with the deformable colloidal particles, for example tethered to the deformable colloidal particles. In such embodiments, the first population of the AOI will usually penetrate less deeply into the skin than the second population of the AOI, providing effects at different depths of tissue.

Where the composition of the first aspect of the present invention comprises two such populations of the same AOI, the proportion of the first population to the second population is designed according to the separate purposes that each of the populations is designated to perform. Preferably, the ratio of the first population to the second population is within the range 20:80 to 80:20, 30:70 to 70:30, 40:60 to 60:40 or approximately 50:50.

The AOI may be selected from the group consisting of an element, an ion, an inorganic salt, a small molecule, an amino acid, a peptide, a protein, a carbohydrate, a lipid, a micronutrient, a macromolecule or a macrocyclic molecule.

The AOI may be a skin structural protein (such as elastin or collagen), a therapeutic protein, porphyrin or chromophore containing a macromolecule, a vitamin (such as vitamin C, D or E), titanium dioxide, zinc oxide, zinc stearate, melanin or a melanin analogue. The AOI may be a peptide or a synthetic organic chemical such as an anti-inflammatory drug, for example an NSAID.

Preferably, the AOI is a biologically active agent. As used herein, the phrase biologically active agent includes but is not limited to pharmaceutically active agents. A biologically or pharmaceutically active agent is herein defined as an agent that has pharmacological, metabolic or immunological activity. To be termed a biologically active agent, the agent in question must be present in the composition in a concentration sufficient and appropriate to achieve a therapeutic or cosmetic effect when administered to a patient. Biologically active agents may include nutraceuticals, cosmetic agents or pharmaceuticals. The AOI has preferably received regulatory approval.

The biologically active agent may be an antiseptic, an antibiotic, an anaesthetic, an analgesic, a skin lightener, and antihistamine, a steroid, an anti-inflammatory agent, an anti-viral, sun block, moisturizer, nicotine, anti-fungal, anti-microbial, nutraceuticals, an essential oil or a hormone.

Preferably, the biologically active agent is selected from the group including but not limited to chlorhexidine or a salt thereof, capsaicin, salicylic acid or a salt or ester thereof, glucosamine or a salt thereof, an amide of glucosamine or a salt thereof, chondroitin or a salt thereof, caffeine and tocopherol or a derivative thereof.

Chlorhexidine, N,N""1,6-Hexanediylbis[N'-(4-chlorophenyl)(imidodicarbonimidic diamide)], is a cationic polybiguanide (bisbiguanide). It is an antimicrobial compound that is effective against a wide range of gram-positive and gram-negative bacteria and some fungi and viruses. It is widely used in topical disinfectants, cosmetics and pharmaceutical products, including wound dressings and mouthwashes. It is also used for the treatment of acne.

Chlorhexidine may be used in the form of a salt. Preferably, the salt of chlorhexidine is selected from the group consisting of chlorhexidine dihydrochloride, chlorhexidine diacetate, chlorhexidine gluconate and chlorhexidine digluconate. Most preferably, the composition comprises chlorhexidine digluconate.

The compositions of the present invention may comprise about 0.1 to 3.0% chlorhexidine or a salt thereof by weight, about 1.0 to 3.0% by weight, about 2.0 to 3.0% by weight, about 0.1 to 2.0% by weight, about 1.0 to 2.0% by weight, approximately 1.5% by weight, about 0.1 to 1.0% by weight, about 0.1 to 0.5% by weight, or approximately 0.3% by weight. Preferably, the compositions of the present invention comprise comprises chlorhexidine or a salt thereof at a concentration below its critical micelle concentration.

Preferably, the chlorhexidine or salt thereof is present in the composition in the form of insoluble aggregates or micelles. Where the AOI comprises chlorhexidine or a salt thereof, the continuous phase is preferably aqueous.

Exemplary compositions according to the first aspect of the present invention comprising chlorhexidine or salt thereof are provided in Example 2.

Capsaicin, 8-methyl-N-vanillyl-6-nonenamide, is a capsaicinoid which is produced as a secondary metabolite by the fruits of plants in the genus *Capsicum*, including chilli peppers. It is believed to act as a deterrant against predation by certain mammals and also as an anti-fungal agent. In medicine, capsaicin is used as an analgesic, particularly for the temporary relief of pain associated with arthritis, backache, strains and sprains, fibromyalgia and neuralgia. It is also used to reduce itching and inflammation associated with conditions such as psoriasis.

The compositions of the present invention may comprise about 0.01 to 0.1% capsaicin by weight, more preferably about 0.01 to 0.05% by weight, most preferably approximately 0.025% by weight.

The capsaicin may be dissolved in the continuous phase, when the continuous phase comprises a suitable solvent, for example ether, benzene and/or an alkane.

Preferably, the capsaicin is present in the composition in the form of insoluble aggregates or associated with non-deformable colloidal particles such as liposomes comprising one or more phospholipids. Preferably, the capsaicin is bound in the liposome membrane. Under such circumstances, the continuous phase is preferably aqueous.

Exemplary compositions according to the first aspect of the present invention comprising capsaicin thereof are provided in Example 3.

Salicylic acid is a beta hydroxy acid (BHA) with the formula $C_6H_4(OH)COOH$. It can be obtained from the bark of willow trees. Salicylic acid is an important active metabolite of aspirin (acetylsalicylic acid), which acts in part as a prodrug to salicylic acid. It is widely used as an analgesic and it also has anti-inflammatory, anti-pyretic, anti-diabetic, bactericidal and antiseptic effects. As a result, it is an important ingredient in pain-killers, topical anti-acne products, rubefacient products, skin-care products for the treatment of conditions such as psoriasis, calluses, ichthyosis and warts, shampoos for the treatment of dandruff, suntan and sunscreen products, mouthwashes and dentifrices. It can also be used for the prevention or treatment of uneven skin tone caused by, for example, darker melanic spots and liver spots.

Salicylic acid can be used in the above applications in the form of a salt or ester. Salts of salicylic acid include calcium salicylate, magnesium salicyalte, MEA-salicylate, potassium salicylate, sodium salicylate and TEA-salicylate. Esters of salicylic acid include butyloctyl salicylate, C12-15 alkyl salicylate, capryolyl salicylic acid, hexyldecyl salicylate, isocetyl salicylate, isodecyl salicylate, ethylhexyl salicylate, methyl salicylate, myristyl salicylate and tridecyl salicylate.

Preferably, the composition of the first aspect of the present invention comprises an ester of salicylic acid, most preferably myristyl salicylate or tridecyl salicylate.

The compositions of the present invention may comprise salicylic acid or a salt or ester thereof in concentrations appropriate to the intended use and within any regulatory limitations. Preferably, the compositions of the present invention comprise salicylic acid or a salt or ester thereof in a concentration sufficient and appropriate to achieve the intended therapeutic or cosmetic effect when administered to a patient.

The compositions of the present invention preferably comprise about 0.05 to 2.5% by weight of salicylic acid or a salt or ester thereof, including myristyl salicylate and tridecyl salicylate, preferably 0.05 to 2.0% by weight, 0.05 to 1.0% by weight, 0.05 to 0.5% by weight, 0.05 to 0.2% by weight, approximately 0.1% by weight, 0.1 to 2.0% by weight, 0.1 to 2.5% by weight or 0.2 to 1.8% by weight.

Salicylic acid and salts and esters thereof are water soluble and thus, where the continuous phase is aqueous, the salicylic acid or salt or ester thereof may be dissolved within the continuous phase. At least some of the salicylic acid or salt or ester thereof may also partition into the membrane of the deformable colloidal particles of the present invention and/or one or more non-deformable colloidal particles also present in the composition.

Glucosamine, or (3R,4R,5S)-3-Amino-6-(hydroxymethyl)oxane-2,4,5-triol, is an amino sugar and a prominent precursor in the biochemical synthesis of glycosylated proteins and lipids. Is commonly used as a dietary supplement, in particular for the treatment of osteoarthritis.

Glucosamine may be used in the form of an amide such as N-acetylglucosamine.

The compositions of the present invention may comprise salts of glucosamine or the amides of glucosamine, such as glucosamine sulfate, glucosamine hydrochloride and N-acetylglucosamine sulphate.

The compositions of the present invention may comprise about 0.01 to 1.0% by weight of glucosamine, amides of glucosamine or salts thereof, more preferably about 0.05 to 0.5% by weight, more preferably about 0.1 to 0.3% by weight, most preferably approximately 0.2% by weight.

Glucosamine, amides of glucosamine and salts thereof are water soluble. Thus, where the continuous phase of the composition is aqueous, these may be dissolved within the continuous phase.

Chondroitin is a glycosaminoglycan (GAG) composed of a chain of alternating sugars, N-acetylgalactosamine and glucuronic acid. It is usually found attached to proteins as part of a proteoglycan. A chondroitin chain can have over 100 individual sugars, each of which can be sulfated in variable positions and quantities.

Chondroitin may be used in the form of a salt, such as chondroitin sulphate, chondroitin gluconate and chondroitin hydrochloride. Chondroitin sulfate is an important structural component of cartilage and has become a widely used dietary supplement for treatment of osteoarthritis.

The compositions of the present invention may comprise about 0.01 to 1.0% chondroitin or salts thereof by weight, more preferably about 0.05 to 0.5% by weight, more preferably about 0.1 to 0.3% by weight, most preferably approximately 0.2% by weight.

Chondroitin and salts thereof, such as chondroitin sulphate, are water soluble. Thus, where the continuous phase of the composition is aqueous, these may be dissolved within the continuous phase.

Exemplary compositions according to the first aspect of the present invention comprising glucosamine, amides of glucosamine or salts thereof and chondroitin or salts thereof are provided in Example 4.

Caffeine, or 1,3,7-Trimethylpurine-2,6-dione, is a methylxanthine alkaloid which is naturally found in the seeds, nuts, or leaves of a number of plants native to South America and East Asia. Whilst commonly used as a stimulant of the central nervous system, caffeine is also a powerful antioxidant and anti-inflammatory that can be topically applied to reduce wrinkles, eye puffiness and dark under-eye circles. It may also be used to prevent sun damage to the skin.

The compositions of the present invention may comprise about 0.001 to 1.0% caffeine by weight, more preferably about 0.01 to 0.5% by weight, more preferably about 0.02 to 0.1% by weight, more preferably about 0.02 to 0.08% by weight, most preferably approximately 0.05% by weight.

Caffeine is water soluble. Thus, where the continuous phase of the composition is aqueous, caffeine may be dissolved within the continuous phase. At least some of the caffeine may also partition into the membrane of the deformable colloidal particles of the present invention and/or one or more non-deformable colloidal particles also present in the composition.

Exemplary compositions according to the first aspect of the present invention comprising caffeine are provided in Example 5.

Tocopherols are a class of organic chemical compounds (more precisely, various methylated phenols), many of which have vitamin E activity. There are four different forms of tocopherol; alpha, beta, gamma and delta. Tocopherols have a number of functions within the body. They have antioxidant and anti-inflammatory effects, which help protect cells from the damaging effects of free radicals which can lead to cardivascular disease and cancer. Tocopherols are involved in healthy immune function, gene expression, blood circulation, protecting the health of nerves and preventing mental degeneration. Tocopherols also have an important role in skin care, protecting the skin from oxidative damage resulting from UV rays and pollution. Topical application of tocopherols can help reduce redness, sunburn and skin damage, including UV-induced tumour formation. Tocopherols also help to protect the cells that make collagen and elastin, providing an anti-ageing effect. Tocopherols are also effective moisturizers, hydrating the skin and preventing further water loss, aiding in the reduction of fine lines and wrinkles. Tocopherols also reduce the healing time of wounds and can be used to help repair skin lesions and dry skin and treat skin conditions such as psoriasis and erythema.

Alpha-tocopherol is the form of vitamin E that is preferentially absorbed and accumulated in humans.

Tocopherol, preferably alpha-tocopherol, may be present in the continuous phase of the compositions of the present invention (as "free" tocopherol).

Tocopherols may be used in the form of one or more isomers or enantiomers or a racemic mixture thereof.

The compositions of the present invention may comprise about 0.01 to 1.0% by weight of "free" tocopherol, such as alpha tocopherol, more preferably 0.05 to 0.5% by weight, more preferably 0.1% to 0.3% by weight, most preferably approximately 0.2% by weight. A small amount of the "free" tocopherol may partition into the lumen of the deformable colloidal particles, but a significant amount will remain in the continuous phase.

Exemplary compositions according to the first aspect of the present invention comprising alpha tocopherol in the continuous phase are provided in Example 6.

Derivatives of tocopherols, for example esters such as tocopheryl linoleate, may also be used. Such derivatives may be tethered to the deformable colloidal particles in various compositions of the present invention, as discussed herein.

The compositions of the present invention may comprise more than one AOI that is not associated with the deformable colloidal particles. For example, a preferred composition of the present invention comprises glucosamine or a salt thereof and/or an amide of glucosamine or a salt thereof, in combination with chondroitin or a salt thereof. For example, the composition of the present invention may comprise glucosamine hydrochloride and/or N-acetylglucosamine sulphate in combination with chondroitin sulphate.

As discussed above, the compositions of the present invention comprise deformable colloidal particles comprising a surfactant and optionally a phospholipid.

As well as facilitating the absorption of the AOI into the skin, the deformable colloidal particles of the present invention can themselves elicit a therapeutic effect. For example, vesicles according to the present invention have been demonstrated to facilitate lipid clearance from the skin by removing sebum, which is beneficial for the treatment of oily skin conditions including acne. The vesicles have also been shown to alleviate or attenuate pain upon topical application. For example, as described in WO 2010/140061, the vesicles have been demonstrated to relieve the pain associated with osteoarthritis. Following topical applications, the vesicles penetrate the skin and are delivered to the underlying muscle tissue and joint, providing a lubricating effect. It is also hypothesized that the movement of the deformable colloidal particles through the skin, into the extracellular interstitial spaces and ultimately into the lymph nodes, facilitates drainage of the interstitial fluids to the lymph. Enhanced drainage of the interstitial fluid assists in the removal of undesirable by-products from tissues, preventing toxic build-up of by-products. This can be of benefit to the appearance of the skin.

Without wishing to be bound by theory, it is believed that the compositions of the invention are able to achieve these functions through the unique properties of colloid particles, which are particles composed of surfactant and/or lipid, such as phospholipid. The uniqueness of the colloid particles derives from the inclusion in the composition of a specific amount of surfactant, preferably non-ionic surfactant, which results in a highly deformable colloidal particle. Where the colloidal particle comprises a lipid such as a phospholipid, the surfactant modifies the lipid membrane to such an extent that the resulting particles are in a permanent liquid crystalline state. Since the surfactant also confers membrane stability, the particles are ultra-deformable, robust and stable (have reduced rigidity without breaking).

The composition forms into deformable colloidal particles suspended in a suspension medium, for example an aqueous buffer. The particles are highly hydrophilic and this property, together with their ultra-deformability, is key to their ability to be transported across the skin. When the composition of the invention is applied to the skin and allowed to dry, the rehydration driving force of the particles combined with their deformability gives rise to movement of the particles to areas of higher water content on and below the skin permeability barrier. This drives their movement through skin pores and intracellular gaps. The specific ratio of lipid/phospholipid to surfactant facilitates transdermal delivery of particles. As the deformable colloidal particles move through the skin, they push or pull the AOI with them, increasing the speed, depth and effectiveness of absorption of the agents.

As used herein, the term "deformable" refers to the ability of the colloidal particles to easily change their properties, such as shape, elongation ratio and surface to volume ratio. The colloidal particles of this invention may be characterized by their ability to adjust their shape and properties to the anisotropic stress caused by crossing narrow pores in a semipermeable barrier such as the skin. Sufficient deformability implies that a colloidal particle can sustain different unidirectional forces or stress, such as one caused by pressure, without extensive fragmentation, which defines a "stable" colloidal particle.

A "barrier" in the context of this invention is a body with through-extending narrow pores, such narrow pores having a radius which is at least 25% smaller than the radius of the colloidal particles (considered as spherical) before said colloidal particles permeate through such pores.

The term "narrow" used in connection with a pore implies that the pore radius is significantly, typically at least 25%, smaller than the radius of the colloidal particle tested with regard to its ability to cross the pore. The necessary difference typically should be greater for the narrower pores. Using 25% limit is therefore quite suitable for >150 nm diameter whereas >100% difference requirement is more appropriate for the smaller systems, e.g., with <50 nm diameter.

Preferably, the deformability of the colloidal particles may be determined by the ability of the colloidal particles to penetrate a barrier with pores having an average pore diameter at least 25%, at least 30%, at least 35%, at least 40%, at least 55%, at least 50%, at least 55% or at least 60% smaller than the average particle diameter before the penetration. Most preferably, the deformability of the colloidal particles may be determined by the ability of the colloidal particles to penetrate a barrier with pores having an average pore diameter at least 50% smaller than the average particle diameter before the penetration.

The term "semipermeable" used in connection with a barrier implies that a solution can cross transbarrier openings whereas a suspension of non-adaptable aggregates (large enough for the above definition of "narrow" pores to apply) cannot. Conventional lipid vesicles (liposomes) made from any common phosphatidylcholine in the gel lamellar phase or else from any biological phosphatidylcholine/cholesterol 1/1 mol/mol mixture or else comparably large oil droplets, all having the specified relative diameter, are three examples for such non-adaptable aggregates.

The term "stable" means that the colloidal particles do not change their diameter spontaneously or under the transport related mechanical stress (e.g. during passage through a semipermeable barrier) unacceptably, which most often means only to a pharmaceutically acceptable degree. A 20-40% change is normally considered acceptable; the halving or doubling of the diameter of the colloidal particles is borderline and a greater change in diameter is typically unacceptable. Alternatively and very conveniently, the change in diameter of the colloidal particles resulting from pore crossing under pressure is used to assess system stability; the same criteria are then applied as for "narrow" pores, mutatis mutandis. To obtain the correct value for diameter change, a correction for flux/vortex effects may be necessary. These procedures are described in greater detail in the publications of the applicant in Cevc et. al., Biochim. Biophys. Acta 2002; 1564:21-30.

Non-destructing passage of colloidal particles through narrow pores in a semi-permeable barrier is thus diagnostic of deformability. If pore radius is two times smaller than the average radius of the colloidal particles, the colloidal particles must change their shape and surface-to-volume ratio at least 100% to pass without fragmentation through the barrier. An easy and reversible change in shape inevitably implies high deformability of the colloidal particles and requires large surface-to-volume ratio adaptation. A change in surface-to-volume ratio per se implies: a) high volume compressibility, e.g. in the case of compact droplets containing material other than, and immiscible with, the suspending fluid; b) high membrane permeability, e.g. in the case of colloidal particles that are free to exchange fluid between inner and outer vesicle volume.

Methods of testing deformability which may be used to characterise the compositions of the invention are set forth in WO 2010/140061 and US Patent Application Nos. 2004/0071767 and 2004/0105881, each herein incorporated by reference as if set forth herein in their entirety.

The deformable colloidal particles may comprise one or more surfactants and no phospholipids, or one or more surfactants in combination with one or more phospholipids.

Preferably, the deformable colloidal particles comprise at least one surfactant and at least one phospholipid. A surfactant is included in order to provide colloidal particles which are in a permanent liquid crystalline state and which are highly hydrophilic, ultra-deformable, robust and stable.

Preferably, these deformable colloidal particles comprise a fluid core, for example an aqueous core, enclosed by a membrane, for example a bilayer membrane. Suitable bilayer membranes include phospholipid-surfactant bilayer membranes, non-ionic surfactant bilayer membranes and surfactant-cholesterol bilayer membranes. Preferably, the deformable colloidal particles comprise vesicles. Particularly preferred vesicles include Sequessomes™, Transfersomes™ and Tethersomes. Usually, the term "Transfersome™" is used to refer to a deformable phospholipid and surfactant vesicle which is associated with an AOI, in particular where the AOI is either held in the lumen of the vesicle or bound within the vesicle's membrane. As described herein, the term "Sequessome™" is usually used to refer to the deformable phospholipid and surfactant vesicle itself. If an AOI is 'tethered' to the vesicle, such that it is held outside the external surface of the membrane, the vesicle (or Sequessome™) may be referred to as a 'Tethersome'. The deformable colloidal particles may also comprise niosomes.

Preferably, the deformable colloidal particles are approximately 60 nm to 200 nm in diameter, preferably 100 to 150 nm in diameter, most preferably approximately 120 nm in diameter.

Deformable colloidal particles of this invention are described in both WO 2010/140061 and WO 2011/022707, each herein incorporated by reference as if set forth herein in their entirety.

The deformable colloidal particles may not be associated with any known AOI i.e. any non-phospholipid, non-surfactant, AOI. For example, the deformable colloidal particles may not be associated with any known biologically active agent. Such deformable colloidal particles may be termed "empty" or "drug-free" deformable colloidal particles. For the avoidance of doubt, references herein to "drug-free" or "empty" deformable colloidal particles are to deformable colloidal particles that do not contain any non-lipid non-surfactant AOI that has a therapeutic purpose. These colloidal particles or colloidal dispersions may comprise active agents such as antimicrobials, stabilisers and preservatives. However, it is to be understood that these agents are simply for improving the stability of the formulations and for increasing their shelf-life; they do not have a therapeutic purpose.

Alternatively, the deformable colloidal particles may be associated with a known AOI, such as a known biologically active agent. The AOI associated with the deformable colloidal particles may or may not be the same as the AOI that is also found in the composition in a form not associated with the deformable colloidal particles. As discussed above, whilst all of the compositions of the present invention comprise an AOI which is not associated with the deformable colloidal particles, some of the same AOI may partition into, or otherwise be associated with, the deformable colloidal particles. Alternatively, the deformable colloidal particles may comprise one or more different, additional AOIs.

The additional AOI associated with the deformable colloidal particles may be an element, an ion, a small molecule, a carbohydrate, a lipid, an amino acid, a peptide, a protein, a macromolecule, a macrocyclic molecule or a micronutrient.

The additional AOI associated with the deformable colloidal particles may be a skin structural protein (such as elastin or collagen), a therapeutic protein, porphyrin or chromophore containing macromolecule, a vitamin, titanium dioxide, a compound comprising zinc such as zinc oxide or zinc stearate, melanin or a melanin analogue. The additional ingredient may be a peptide or an anti-inflammatory drug, such as an NSAID. Specifically, it may be tetrapeptide-7, tripeptide-1, ascorbic acid, palmitoyl ascorbate, tocopheryl lineoleate, myristyl salicylate, tridecyl salicylate, menthol, Naproxen or Diclofenac.

An AOI associated with the deformable colloidal particles may be bonded to its external surface. Where a plurality of additional ingredients or AOIs are bonded, the additional ingredients may all be the same, i.e. homogenous, or be different, i.e. heterogeneous. Methods of tethering ingredients to the external surface of deformable colloidal particles are described in WO 2015/014965, which is herein incorporated by reference.

Additional ingredients or AOIs may also be incorporated into the membrane of the deformable colloidal particle.

Where the composition according to the first aspect of the invention comprises chlorhexidine or a salt thereof as an AOI which is not associated with the deformable colloidal particles, the deformable colloidal particles preferably comprise zinc or a compound comprising zinc, such as zinc oxide or zinc stearate, tethered thereto. Zinc down-regulates sebum production by sebaceous glands and is therefore a useful additional ingredient in compositions for use in the treatment or prevention of acne.

Where the composition of the first aspect of the invention comprises capsaicin as an AOI, the membranes of the deformable colloidal particles preferably comprise menthol.

Where the composition according to the first aspect of the present invention comprises salicylic acid or a salt or ester thereof as an AOI which is not associated with the deformable colloidal particles, the composition may additionally comprise salicylic acid or a salt or ester thereof associated with the deformable colloidal particles. Preferably, this salicylic acid or a salt or ester thereof is tethered to the deformable colloidal particles. Myristyl salicylate or tridecyl salicylate are preferred. The tethered salicylic acid or salt or ester thereof will penetrate to the stratum basale where it will exert an anti-tyrosinase action to down-regulate melanin production. The salicylic acid or salt or ester thereof which is not associated with the colloidal particles will penetrate less deeply into the skin, remaining in the outer layers of the epidermis where it will exert a mild exfoliating effect which will increase the speed of turnover of new, now de-melanised, skin.

Where the composition according to the first aspect of the invention comprises tocopherol or a derivative thereof as an AOI which is not associated with the deformable colloidal particles, the composition may additionally comprise salicylic acid or a salt or ester thereof associated with the deformable colloidal particles. Preferably, this salicylic acid or a salt or ester thereof is tethered to the deformable colloidal particles. Myristyl salicylate or tridecyl salicylate are preferred. As described above, the tethered salicylic acid or salt or ester thereof will penetrate to the stratum basale where it will exert an anti-tyrosinase action to down-regulate melanin production.

The compositions of the present invention may comprise one or more vitamins. These vitamins may be tethered to the colloidal particles, present in the continuous phase or as a separate phase.

Such vitamins may include vitamin C (ascorbic acid) or esters thereof, for example palmityol ascorbic acid or palmitoyl ascorbate. The compositions may comprise 0.01 to 1.0% by weight vitamin C (ascorbic acid) or esters thereof, more preferably 0.05 to 0.5% by weight, most preferably approximately 0.1% by weight. Preferably, the vitamin C or esters thereof are tethered to the deformable colloidal particles.

Another preferred vitamin for inclusion in compositions of the present invention is vitamin E (tocopherol) or esters thereof, for example tocopheryl linoleate. The compositions may comprise 0.01 to 1.0% by weight vitamin E (tocopherol) or esters thereof, more preferably 0.05 to 0.5% by weight, most preferably 0.1% to 0.2% by weight. Preferably, the tocopherol linoleate is tethered to the deformable colloidal particles. Preferably, tocopherol is present as a separate phase.

Vitamins such as vitamin C and vitamin E and esters thereof provide the deformable colloidal particles with an anti-oxidant protective effect.

Compositions of the present invention may comprise both vitamin C and vitamin E or esters thereof. The vitamin C or esters thereof and the vitamin E or esters thereof, where present, may be tethered to separate deformable colloidal particles or to the same deformable colloidal particles.

The tethering of such vitamins is particularly preferred when the AOI which is not associated with the deformable colloidal particles comprises salicylic acid or a salt or ester thereof, glucosamine or a salt thereof, an amide of glucosamine or a salt thereof, chondroitin or a salt thereof, caffeine and tocopherol or derivatives thereof.

Preferably, when the composition comprises salicylic acid or a salt or ester thereof, palmitoyl ascorbic acid and/or tocopheryl linoleate are tethered to the deformable colloidal particles and tocopherol or a derivative thereof is present as a separate phase. Preferably, the composition comprises two forms of deformable colloidal particle; the first comprising salicylic acid or a salt or ester thereof tethered thereto and the second comprising palmitoyl ascorbic acid and/or tocopheryl linoleate tethered thereto. Again, tocopherol or a derivative thereof may be present as a separate phase.

Preferably, when the composition comprises glucosamine or a salt thereof, an amide of glucosamine or a salt thereof and/or chondroitin or a salt thereof, the composition additionally comprises palmitoyl ascorbate and/or tocopheryl linoleate tethered to the deformable colloidal particles. The inclusion of such vitamins into these compositions enhances the efficacy of these compositions in maintaining and prolonging joint health and treating or preventing joint diseases or the pain associated with poor joint health.

Preferably, when the composition comprises caffeine, palmitoyl ascorbic acid is tethered to the deformable colloidal particles.

Compositions according to the present invention comprising caffeine may also comprise tocopherol or a derivative thereof, which is preferably present as a separate phase.

Preferably, where the composition comprises tocopherol or a derivative thereof as an AOI not associated with the deformable colloidal particles (in the absence of caffeine), the composition additionally comprises palmitoyl ascorbic acid and/or tocopheryl linoleate tethered to deformable colloidal particles. Preferably, the composition comprises both palmitoyl ascorbic acid and tocopheryl linoleate tethered to the same colloidal particles. Where such compositions also comprise tethered salicylic acid or a salt or ester thereof, as described above, the salicylic acid or a salt or ester thereof are preferably tethered to a first form of deformable colloidal particle and the palmitoyl ascorbic acid and tocopheryl linoleate are preferably tethered to a second form of deformable colloidal particle.

Compositions of the present invention may additionally comprise tripeptide-1, preferably palmitoyl tripeptide-1, and/or tetrapeptide-7, preferably palmitoyl tetrapeptide-7, tethered to deformable colloidal particles.

The compositions may comprise 0.0001 to 0.1% by weight of tripeptide-1, preferably palmitoyl tripeptide-1, more preferably 0.001 to 0.01% by weight, more preferably 0.002 to 0.008% by weight, most preferably approximately 0.006% by weight.

The compositions may comprise 0.0001 to 0.01% by weight of tetrapeptide-7, preferably palmitoyl tetrapeptide-7, more preferably 0.001 to 0.01% by weight, more preferably 0.002 to 0.008% by weight, most preferably approximately 0.006% by weight.

The tethering of tripeptide-1 and/or tetrapeptide-7, in particular palmitoyl tripeptide-1 and/or palmitoyl tetrapeptide-7, to deformable colloidal particles is particularly preferred when an AOI which is not associated with the deformable colloidal particles is caffeine.

Preferably, compositions of the present invention comprising caffeine and tocopherol comprise three types of deformable colloidal particle; the first comprising palmitoyl ascorbic acid tethered thereto, the second comprising palmitoyl tripeptide-1 tethered thereto and the third comprising palmitoyl tetrapeptide-7 tethered thereto.

The inclusion of palmitoyl tripeptide-1 and palmitoyl tetrapeptide-7 into these compositions enhances their efficacy by stimulating collagen synthesis, firming the skin and reducing the appearance of wrinkles.

For the avoidance of doubt, references herein to an "Agent of Interest", or "AOI" are to the AOI which is not associated with the deformable colloidal particles, unless explicitly stated otherwise. References to an "additional Agent of Interest" or an "additional AOI" are to a further, different AOI, which may or may not be associated with the deformable colloidal particles.

The composition may be a liquid, cream, lotion, ointment, gel, solution, spray, lacquer or film forming solution.

As a second aspect, the present invention provides a method of making the composition of the first aspect of the invention. Preferably, the method comprises a primary manufacturing step in which a colloidal dispersion is made from an "organic phase" containing alcohol-soluble components and an "aqueous phase" consisting of water-soluble components. During a secondary manufacturing step, this initial dispersion is mixed with a thickener to form a gel with the desired consistency. The AOI is preferably added during this secondary manufacturing step. More than one kind of colloidal dispersion may be introduced such that the final composition comprises more than one kind of colloidal particle. An exemplary method of manufacture is described in Example 1 and FIG. 2.

A third aspect of the present invention provides the composition according to the first aspect of the invention for use in medicine. Preferably, the composition is provided for use in treating or preventing a disease, disorder or condition.

The use for which the composition of the present invention is provided will depend at least in part on the identity of the AOI included in the composition.

Where the AOI comprises chlorhexidine or a salt thereof, the third aspect provides the composition according to the first aspect of the present invention for use in treating or preventing a disease or disorder associated with the skin of a patient. Preferably, the disease or disorder comprises acne or dermatitis. The compositions of the present invention can also be used to treat and care for acne-prone skin, in particular to prevent the appearance of acne in acne-prone skin. The compositions can also be used to treat or prevent the formation of spots, blackheads and blemishes, reduce skin impurities, reduce the spread of infection in the skin and tighten and constrict pores.

The compositions of the present invention provide these benefits, not only because the deformable colloidal particles increase the speed, depth and effectiveness of absorption of the chlorhexidine or salt thereof into the skin of the patient, which provides an effective antimicrobial action to cleanse the skin and remove bacteria, but also because the deformable colloidal particles can facilitate the clearance of lipids from the skin by removing sebum. Furthermore, as discussed above, tethering zinc or zinc compounds such as zinc oxide or zinc stearate to the deformable colloidal particles down-regulates sebum production by sebaceous glands. Sebum can trap dirt and bacteria which are the primary cause of spots and acne.

As demonstrated in Example 2, below, compositions of the present invention comprising chlorhexidine or a salt thereof significantly reduce surface sebum, comedones (blackheads), papules and pustules.

Where the AOI comprises chlorhexidine or a salt thereof, the third aspect also provides the use of a composition according to the first aspect of the present invention for the manufacture of a medicament for the treatment or prevention of acne or dermatitis.

Where the AOI comprises capsaicin, the third aspect provides the composition according to the first aspect of the present invention for use in treating or preventing one or more conditions selected from the group consisting of pain, including muscle pain, and itching. Compositions comprising capsaicin can be used prophylactially, for example being applied prior to exercise to create a warming sensation in the skin and underlying muscles and thus prevent or delay the onset of the sensation of muscle soreness. Compositions comprising capsaicin can also be applied to treat post-exercise muscle pain.

Compositions of the invention comprising capsaicin are also provided for use as an analgesic medicament or an antipruritic medicament.

Where the AOI comprises capsaicin, the third aspect also provides the use of a composition according to the first aspect of the present invention for the manufacture of a medicament for the treatment or prevention of pain or itching.

The compositions of the present invention may be useful for the treatment or prevention of pain, not only because the deformable colloidal particles increase the speed, depth and effectiveness of absorption of the capsaicin into the skin of the patient, but also because the deformable colloidal particles can themselves alleviate or attenuate pain, such as that associated with osteoarthritis, as discussed above.

As demonstrated in Example 3, below, compositions of the present comprising capsaicin provide a pleasant warming sensation when applied to the skin, which lasts for up to one hour.

Where the AOI comprises salicylic acid or a salt or ester thereof, the third aspect provides the composition according to the first aspect of the present invention for use in treating or preventing pain. Such pain may include the pain associated with osteoarthritis and muscle pain such as post-exercise muscle pain. Preferably, the salicylic acid or a salt or ester thereof is present in the composition, both associated with the deformable colloidal particles and not associated with the deformable colloidal particles. Preferably, the salicylic acid or salt or ester therefore which is associated with the deformable colloidal particles is tethered to the deformable colloidal particles.

Where the AOI comprises salicylic acid or a salt or ester thereof, the third aspect also provides the use of a composition according to the first aspect of the present invention for the manufacture of a medicament for the treatment or prevention of pain.

The compositions of the present invention may be useful for the treatment or prevention of pain, not only because the deformable colloidal particles increase the speed, depth and effectiveness of absorption of the salicylic acid or salt or ester thereof into the skin of the patient, but also because the deformable colloidal particles can themselves alleviate or attenuate pain, such as that associated with osteoarthritis, as discussed above.

Compositions according to the present invention containing a salicylate compound may also find use as a counter irritant.

Where the AOI comprises glucosamine or a salt thereof, an amide of glucosamine or a salt thereof, and/or chondroitin or a salt thereof, the third aspect provides the composition according to the first aspect of the present invention for use in maintaining and prolonging joint health and/or for treating or preventing joint diseases (arthropathy), in particular degenerative joint diseases such as arthritis and osteoarthritis. These compositions may also be used to treat or prevent the pain associated with poor joint health.

Where the AOI comprises glucosamine or a salt thereof, an amide of glucosamine or a salt thereof, and/or chondroitin or a salt thereof, the third aspect also provides the use of a composition according to the first aspect of the present invention for the manufacture of a medicament for maintaining and prolonging joint health and/or for treating or preventing joint diseases (arthropathy), in particular degenerative joint diseases such as arthritis and osteoarthritis, or the pain associated with poor joint health.

The compositions of the present invention may be useful for maintaining and prolonging joint health and for treating or preventing joint diseases or the pain associated with poor joint health, not only because the deformable colloidal particles increase the speed, depth and effectiveness of penetration of the AOI into the joint of the patient, but also because the deformable colloidal particles can themselves alleviate or attenuate pain, such as that associated with osteoarthritis, as discussed above.

The compositions of the present invention are particularly suitable for patients with chronic, long-term pain associated with joint diseases such as osteoarthritis, who wish to avoid or minimise the consumption of pharmaceutical painkillers.

Preferably, the composition of the present invention is applied topically to the skin of a patient.

The composition of the invention may be topically applied once, twice, three times or more per day. Alternatively the composition may be administered on alternate days, two or three times per week, once per week or less frequently as needed. The composition may be administered over a period of one or more weeks, for example, for at least one week, two weeks, three weeks, four weeks, five weeks, six weeks, seven weeks, eight weeks, nine weeks, ten weeks, eleven weeks, or twelve weeks, sixteen weeks, twenty four weeks, four months, six months, eight months, ten months, one year, two or more years, or as often as needed within any regulatory restrictions.

Any amount of the composition sufficient to treat the condition in question may be administered to the patient, within any regulatory restrictions applicable to the AOI. For example, a 0.1 to 10 gram dose of the composition of the invention may be administered to the patient. The dose may be 1 to 10 grams, or 1 to 5 grams or about 1 gram, 2 grams, 3 grams, 4 grams, 5 grams, 6 grams, 7 grams, 8 grams, 9 grams or 10 grams. The dose may be measured as the total weight of the composition. The dose can be measured as the total weight of the phospholipid(s) and/or surfactant(s) in the composition. The dose may be administered once or twice daily or as often as needed. The dose may be administered once, twice, three, four, five, six, or seven times per week, or as often as needed, in accordance with the invention. The dose may be administered every day, every other day, or two to three times a week, or as often as needed, in accordance with the invention. Preferably, the composition may be applied twice daily. A suitable amount of the composition (i.e. any amount of the composition sufficient to treat a condition as herein described) may be spread over the problem area of the skin. The composition may be left to dry for up to 10 minutes.

A fourth aspect of the present invention provides a method of treating or preventing a disease, disorder or condition comprising administering the composition of the present invention to a subject or patient in need thereof. Preferably, the composition is topically applied to the skin of the subject or patient.

Where the AOI comprises chlorhexidine or a salt thereof, the disease, disorder or condition is preferably acne or dermatitis.

Where the AOI comprises capsaicin, the disease, disorder or condition is preferably selected from the group comprising pain, including muscle pain, and itching.

Where the AOI comprises salicylic acid or a salt or ester thereof, the disease, disorder or condition is preferably pain.

Where the AOI comprises glucosamine or a salt thereof, an amide of glucosamine or a salt thereof, and/or chondroitin or a salt thereof, the disease, disorder or condition is preferably a joint disease (arthropathy), in particular a degenerative joint disease such as arthritis or osteoarthritis, or the pain associated with poor joint health.

The present invention also provides a method of maintaining and prolonging joint health, comprising topically applying a composition according to the first aspect of the invention to the skin of a patient in need thereof, wherein the AOI comprises glucosamine or a salt thereof, an amide of glucosamine or a salt thereof, and/or chondroitin or a salt thereof.

All preferred features of the third aspect of the invention also apply to the fourth aspect of the invention.

A fifth aspect of the present invention provides the composition according to the first aspect of the invention for use in skin care or cosmetics.

Compositions of the present invention comprising chlorhexidine or a salt thereof can improve the appearance of the skin. As discussed above, they do so by treating or preventing acne and the formation of spots, blackheads and blemishes, reducing skin impurities, reducing the spread of infection in the skin and tightening and constricting pores.

Compositions of the present invention comprising capsaicin have applications in cosmetics through their mild irritant effect. In particular, the topical application of capsaicin to the skin results in vasodilation. When applied to the lips, capsaicin causes the lips to swell and redden. Such compositions may therefore be used to improve the cosmetic appearance of the lips.

Compositions of the present invention comprising salicylic acid or a salt or ester thereof can be used to improve the appearance of uneven skin tone by reducing the appearance of hyperpigmentation such as melanic spots and liver spots. Preferably, the salicylic acid or a salt or ester thereof is present in the composition, both associated with the deformable colloidal particles and not associated with the deformable colloidal particles. Preferably, the salicylic acid or salt or ester therefore which is associated with the deformable colloidal particles is tethered to the deformable colloidal particles.

Such a composition has a dual effect. The tethered salicylic acid or salt or ester thereof will penetrate more deeply into the stratum basale of the epidermis where the melanocytes are located where it will exert an anti-tyrosinase action to down-regulate melanin production. The salicylic acid or salt or ester thereof which is not associated with the deformable colloidal particles will penetrate less deeply into the skin, remaining in the outer layers where it will exert a mild exfoliating effect which will increase the speed of turnover of new, now de-melanised, skin. The skin-lightening effects of the tethered salicylic acid or salt or ester thereof will therefore be seen by the patient more quickly than in the absence of untethered salicylic acid or a salt or ester thereof.

Compositions of the present invention comprising glucosamine or salt thereof, an amide of glucosamine or a salt thereof and/or chondroitin or a salt thereof can be used to improve the appearance of the skin. Chondroitin and glucosamine are important constituents of cartilage and other connective tissue such as collagen. Supplementing the supply of these may be helpful in supporting collagen production and the repair of the structure of the skin and may therefore reduce the appearance of fine lines and wrinkles. They may also improve skin tone, barrier function and hyperpigmentation.

Compositions of the present invention comprising caffeine can improve the appearance of the skin, particularly periorbital skin. As discussed above, they do so by acting as a powerful antioxidant and anti-inflammatory. In particular, caffeine has vasoconstrictor properties and is thought to shrink the blood vessels that cause under-eye dark circles. As demonstrated in Example 5, the compositions of the present invention can reduce the appearance of puffiness and swelling around the eyes and below the lower eyelid (eye bags), under-eye dark circles and fine lines and deep wrinkles, including crow's feet, around the eye area. The compositions can also result in periorbital skin which looks and feels less thin, looks and feels more firm, feels more elastic, looks smoother and which is more hydrated. The compositions can also lift sagged skin, resulting in a reduction in skin droopiness and sagging. The compositions can make the skin tone look more even, make the eye contour look and feel tighter and look more toned and lifted and make the eyes look rested and less tired. They may also be used to prevent sun damage to the skin.

The compositions of the present invention may be useful for improving the appearance of the skin, particularly periorbital skin, not only because the deformable colloidal particles increase the speed, depth and effectiveness of absorption of the caffeine into the skin of the patient, but also because the deformable colloidal particles themselves can improve the appearance of the skin. It is hypothesised, without wishing to be bound by any mechanism of action, that the movement of the deformable colloidal particles through the skin, into the extracellular interstitial spaces and ultimately into the lymph nodes facilitates drainage of the interstitial fluids to the lymph. Enhanced drainage of the interstitial fluid assists in the removal of undesirable by-products from tissues, preventing toxic build-up of by-products.

Where these compositions comprise palmitoyl ascorbic acid and tocopherol or a derivative thereof, their antioxidant effect is enhanced. Where these compositions comprise palmitoyl tripeptide-1 and palmitoyl tetrapeptide-7 tethered to the deformable colloidal particles, collagen synthesis is also stimulated. The appearance of the periorbital skin is therefore further improved.

Compositions of the present invention comprising tocopherol or a derivative thereof in the continuous phase and salicylic acid or a salt or ester thereof tethered to the deformable colloidal particles can improve the appearance of the skin. In particular, the compositions can be used to improve the appearance of skin tone, for example by treating and/or preventing uneven skin tone.

As discussed above, the tocopherol acts as a powerful antioxidant and anti-inflammatory, protecting the cells that make collagen and elastin and acting as an effective moisturizer. As discussed above, salicylic acid or a salt or ester thereof can also improve the appearance of uneven skin tone by reducing the appearance of hyperpigmentation such as melanic spots and liver spots. As demonstrated in Example 6, the compositions of the present invention can reduce the appearance of fine lines and wrinkles and the amount and size of hyperpigmentation/pigmented skin blemishes. The compositions can result in skin which looks significantly smoother and feels significantly more healthy and elastic. The compositions can help the complexion look younger and significantly healthier, be visibly improved and more radiant. The compositions can also make skin tone look significantly more even and significantly lighten hyperpigmentation/pigmented skin blemishes and periorbital dark circles.

Where these compositions comprise palmityol ascorbic acid and tocopheryl linoleate tethered to a second form of deformable colloidal particle, their antioxidant effect is enhanced.

The compositions of the present invention may be useful for improving the appearance of the skin, not only because the deformable colloidal particles increase the speed, depth and effectiveness of absorption of the tocopherol and salicylic acid or salt or ester thereof into the skin of the patient, but also because the deformable colloidal particles themselves can improve the appearance of the skin. As discussed above, the deformable colloidal particles can enhance drainage of the interstitial fluid to the lymph nodes, preventing toxic build-up of by-products in the skin.

A sixth aspect of the present invention provides a method of cosmetically improving the appearance of a subject comprising administering the composition of the present invention to the subject. Preferably, the composition is topically applied to the skin of the subject, who is preferably human.

Where the AOI comprises chlorhexidine or a salt thereof, the method preferably comprises improving the appearance of the skin of the subject, for example by treating or preventing acne.

Where the AOI comprises capsaicin, the method preferably comprises improving the cosmetic appearance of the lips of the subject, for example by plumping the lips.

Where the AOI agent comprises salicylic acid or a salt or ester thereof, the method preferably comprises improving the appearance of uneven skin tone, preferably by reducing the appearance of hyperpigmentation.

Where the AOI comprises glucosamine or salt thereof, an amide of glucosamine or a salt thereof and/or chondroitin or a salt thereof, the method preferably comprises improving the appearance of the skin, for example by supporting collagen production to reduce the appearance of fine lines and wrinkles.

Where the AOI comprises caffeine, the method preferably comprises improving the appearance of the skin of the subject, preferably the periorbital skin.

Where the AOI comprises tocopherol or a derivative thereof in the continuous phase and salicylic acid or a salt or ester thereof tethered to the deformable colloidal particles, the method preferably comprises improving the appearance of the skin, for example by treating and/or preventing uneven skin tone.

All preferred features of the fifth aspect of the invention also apply to the sixth aspect of the invention.

A seventh aspect of the present invention provides a method of delivering an AOI to or through the skin of a patient, the method comprising topically applying to the skin of the patient a composition according to the first aspect of the invention in an amount sufficient to penetrate the skin to deliver the AOI.

The present invention can be used to administer the AOI, such as chlorhexidine or a salt thereof, capsaicin, salicylic acid or a salt or ester thereof, glucosamine or salt thereof, an amide of glucosamine or a salt thereof and/or chondroitin or a salt thereof, caffeine or tocopherol or a derivative thereof, to or through the skin of an animal. Preferably, the method comprises topically applying the composition to the skin of the patient in an amount sufficient to penetrate the skin to deliver the AOI.

The present invention can also be used to administer an AOI, such as glucosamine or a salt thereof, an amide of glucosamine or a salt thereof and/or chondroitin or a salt thereof, to a joint of an animal, for example a shoulder, elbow, wrist, knuckle, knee or ankle joint. Preferably, the method comprises topically applying the composition to the skin of the patient in an amount sufficient to penetrate the skin to deliver the AOI to the underlying joint. Any animal can be included, including humans, dogs, cats, horses, food production animals and pets.

The compositions may be administered in accordance with the fourth, fifth, sixth and seventh aspects of the present invention in the same amounts and with the same frequency and duration as set out above in respect of the third aspect.

An eighth aspect of the present invention provides a package or kit comprising a container comprising the composition according to the first aspect of the invention and instructions for administration of the composition to a subject. Said subject may comprise a patient in need of said composition.

The composition according to the first aspect of the invention is contained within a single compartment of said container. Preferably, the deformable colloidal particles and the AOI are contained only within this single compartment of the package or kit prior to being dispensed from the package or kit. In other words, it is preferred that the deformable colloidal particles and the AOI are not stored in separate compartments within the package or kit, prior to being mixed within the package or kit for administration to the patient. As discussed above, the inventors have found that the compositions of the present invention, comprising both the deformable colloidal particles and the AOI, are surprisingly stable and can be stored ready-mixed in a single compartment of a package or kit.

The kit may be formatted such that the container is marked to indicate quantity of the composition remaining or dispensed.

The container may be in the form of a tube, sachet or pot. The kit may also comprise a dispensing means, preferably selected from group consisting of a pump, nozzle, measuring cup or spatula.

The instructions for administration of the composition according to the first aspect of the invention preferably comprise instructions for the administration of the composition in accordance with any of the third, fourth, fifth, sixth or seventh aspects of the present invention.

Preferably, the instructions comprise instructions for the topical application of the composition.

Where the AOI comprises chlorhexidine or a salt thereof, the instructions for administration thereof preferably comprise instructions for administration thereof to a patient or subject in need thereof for the treatment or prevention of a disease or disorder associated with the skin of a patient, preferably acne or dermatitis. The instructions may alternatively direct the subject to administer the composition to the skin for the purpose of improving its appearance.

Where the AOI comprises capsaicin, the instructions for administration thereof preferably comprise instructions for administration thereof to a patient or subject in need thereof for the treatment or prevention of pain, including muscle pain, and/or itching. The instructions may also direct the subject to administer the composition prior to exercise. The instructions may alternatively direct the subject to administer the composition to the lips for the purpose of providing a cosmetic "plumped" effect.

Where the AOI comprises salicylic acid or a salt or ester thereof, the instructions for administration thereof preferably comprise instructions for administration thereof to a patient or subject in need thereof for the treatment or prevention of pain. The instructions may alternatively direct the subject to administer the composition to the skin for the purpose of improving the appearance of uneven skin tone, including hyperpigmentation.

Where the AOI comprises glucosamine or salt thereof, an amide of glucosamine or a salt thereof, and/or chondroitin or a salt thereof, the instructions for administration thereof preferably comprise instructions for administration thereof to a patient or subject in need thereof for maintaining and prolonging joint health and/or for treating or preventing joint diseases (arthropathy), in particular degenerative joint diseases such as arthritis and osteoarthritis, or the pain associated with poor joint health. The instructions may alternatively direct the subject to administer the composition to the skin for the purpose of improving the appearance of the skin, for example by reducing the appearance of fine lines and wrinkles and improving the appearance skin tone, barrier function and hyperpigmentation.

Where the AOI comprises caffeine, the instructions for administration thereof preferably comprise instructions for administration thereof to a patient or subject in need thereof for improving the appearance of the skin, for example the periorbital skin.

Where the AOI comprises tocopherol or a derivative thereof in the continuous phase and salicylic acid or a salt or ester thereof tethered to the deformable colloidal particles, the instructions for administration thereof preferably comprise instructions for administration thereof to a patient or subject in need thereof for improving the appearance of the skin, for example treating and/or preventing uneven skin tone.

A ninth aspect of the present invention comprises a transdermal drug release device comprising a support layer and a layer comprising the composition according to the first aspect of the present invention.

The transdermal drug release device may comprise a strip, plaster, bandage or patch.

The support layer may be made of any suitable material including fabric and silicon.

The transdermal drug release device may be applied to the skin of a patient such that the layer of the composition of the first aspect of the invention is in contact with the skin of the patient.

The support layer may remain on the skin for a set period of time, for example 1 hour to 3 days. Alternatively, the support layer may be removed and the composition layer may remain in contact with the skin.

All of the preferred features of each aspect of the invention apply mutatis mutandis to all other aspects of the invention.

Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs.

In accordance with this disclosure, the term "comprising" is inclusive or open-ended and does not exclude additional, unrecited elements or method steps; the term "consisting of" excludes any element, step, or ingredient not specified; and the term "consisting essentially of" excludes any element, step, or ingredient that materially changes a basic characteristic of the invention As used herein, a "sufficient amount", "amount effective to" or an "amount sufficient to" achieve a particular result refers to an amount of the composition of the invention is effective to produce a desired effect, which is optionally a therapeutic effect (i.e., by administration of a therapeutically effective amount). Alternatively stated, a "therapeutically effective" amount is an amount that provides some alleviation, mitigation, and/or decrease in at least one clinical symptom. Clinical symptoms associated with the disorder that can be treated by the methods of the invention are well-known to those skilled in the art. Further, those skilled in the art will appreciate that the therapeutic effects need not be complete or curative, as long as some benefit is provided to the subject.

As used herein, the terms "treat", "treating" or "treatment of" mean that the severity of a subject's condition is reduced or at least partially improved or ameliorated and/or that some alleviation, mitigation or decrease in at least one clinical symptom is achieved and/or there is an inhibition or delay in the progression of the condition and/or delay in the progression of the onset of disease or illness. The terms "treat", "treating" or "treatment of" also means managing the disease state.

As used herein, the term "pharmaceutically acceptable" when used in reference to the compositions of the invention denotes that a composition does not result in an unacceptable level of irritation in the subject to whom the composition is administered. Preferably such level will be sufficiently low to provide a composition suitable for approval by regulatory authorities.

As used herein with respect to numerical values, the term "about" or "approximately" means a range surrounding a particular numeral value which includes that which would be expected to result from normal experimental error in making a measurement. For example, in certain embodiments, the term "about" when used in connection with a particular numerical value means +−20%, unless specifically stated to be +−1%, +−2%, +−3%, +−4%, +−5%, +−10%. +−15%, or +−20% of the numerical value.

The term "alkyl" refers to a linear or branched saturated monovalent hydrocarbon radical, wherein the alkyl may optionally be substituted with one or more substituents Q as described herein. The term "alkyl" also encompasses both linear and branched alkyl, unless otherwise specified. In certain embodiments, the alkyl is a linear saturated monovalent hydrocarbon radical that has 1 to 20 ($C_{1-20}$), 1 to 15 ($C_{1-15}$), 1 to 12 ($C_{1-12}$), 1 to 10 ($C_{1-10}$), or 1 to 6 ($C_{1-6}$) carbon atoms, or a branched saturated monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl". Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms. It is understood in the chemical arts, that the use of the longer chains described herein may be appropriate, or appropriate only in limited amounts, within a molecule so that the properties of the resulting molecule (such as solubility) are appropriate for the use. Thus, while those in the art may use the above longer length alkyl substituents they will be used only when appropriate to provide the desired function.

The term "aryl" refers to a monocyclic aromatic group and/or multicyclic monovalent aromatic group that contain at least one aromatic hydrocarbon ring. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In certain embodiments, aryl may also be optionally substituted with one or more substituents Q as described herein.

The term "heteroaryl" refers to a monocyclic aromatic group and/or multicyclic aromatic group that contain at least one aromatic ring, wherein at least one aromatic ring contains one or more heteroatoms independently selected from O, S. and N. Each ring of a heteroaryl group can contain one or two O atoms, one or two S atoms, and/or one to four N atoms, provided that the total number of heteroatoms in each ring is four or less and each ring contains at least one carbon atom. The heteroaryl may be attached to the main structure at any heteroatom or carbon atom which results in the creation of a stable compound. In certain embodiments, the heteroaryl has from 5 to 20, from 5 to 15, or from 5 to 10 ring atoms. Examples of monocyclic heteroaryl groups include, but are not limited to, pyrrolyl, pyrazolyl, pyrazolinyl, imidazolyl, oxazolyl, isoxazolyl, thiazolyl, thiadiazolyl, isothiazolyi. furanyl. thienyl, oxadiazolyl, pyridyl, pyrazinyl, pyrimidinyl, pyridazinyl, and triazinyl. Examples of bicyclic heteroaryl groups include, but are not limited to, indolyl, benzothiazolyl, benzoxazolyl, benzothienyl, quinolinyl, tetrahydroisoquinolinyl, isoquinolinyl, benzimidazolyl, benzopyranyl, indolizinyl, benzofuranyl, isobenzofuranyl, chromonyl, coumarinyl, cinnolinyl, quinoxalinyl, indazolyl, purinyl, pyrrolopyridinyl, furopyridinyl, thicnopyridinyl, dihydroisoindolyl, and tetrahydroquinolinyl. Examples of tricyclic heteroaryl groups include, but are not limited to carbazolyl, benzindolyl, phenanthrollinyl, acridinyl, phenanthridinyl, and xanthenyl. In certain embodiments, heteroaryl may also be optionally substituted with one or more substituents Z as described herein.

The term "alkenoyl" as used herein refers to —C(O)-alkenyl. The term "alkenyl" refers to a linear or branched monovalent hydrocarbon radical, which contains one or more, in one embodiment, one to five, carbon-carbon double bonds. The alkenyl may be optionally substituted with one or more substituents Z as described herein. The term "alkenyl" also embraces radicals having "cis" and "trans" configurations, or alternatively, "Z" and "E" configurations, as appreciated by those of ordinary skill in the art. As used herein, the term "alkenyl" encompasses both linear and branched alkenyl, unless otherwise specified. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 30 ($C_{2-30}$, 2 to 24 ($C_{2-24}$), 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms, or a branched monovalent hydrocarbon radical of 3 to 30 ($_{3-30}$), 3 to 24 ($C_{3-24}$), 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl. In certain embodiments, the alkenoyl is mono-alkenoyl, which contains one carbon-carbon double bond. In certain embodiments, the alkenoyl is di-alkenoyl, which contains two carbon-carbon double bonds. In certain embodiments, the alkenoyl is poly-alkenoyl, which contains more than two carbon-carbon double bonds.

The term "heterocyclyl" or "heterocyclic" refers to a monocyclic non-aromatic ring system and/or multicyclic ring system that contains at least one non-aromatic ring, wherein one or more of the non-aromatic ring atoms are heteroatoms independently selected from O, S, or N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. In certain embodiments, the heterocyclyl is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, and some rings may be partially or fully saturated, or aromatic. The heterocyclyl may be attached to the main structure at any heteroatom or carbon atom which results in the creation of a stable compound.

Examples of such heterocyclic radicals include, but are not limited to, acridinyl, azepinyl, benzimidazolyl, benzindolyl, benzoisoxazolyl, benzisoxazinyl, benzodioxanyl, benzodioxolyl, benzofuranonyl, benzofuranyl, benzonaphthofuranyl, benzopyranonyl, benzopyranyl, benzotetrahydrofuranyl, benzotetrahydrothienyl, benzothiadiazolyl, benzothiazolyl, benzothiophenyl, benzotriazolyl, benzothiopyranyl, benzoxazinyl, benzoxazolyl, benzothiazolyl, [beta]-carbolinyl, carbazolyl, chromanyl, chromonyl, cinnolinyl, coumarinyl, decahydroisoquinolinyl, dibenzofuranyl, di hydrobenzisothiazi nyl. di hydrobenzisoxazinyl, di hydrofuryl, dihydropyranyl, dioxolanyl, di hydropyrazinyl, dihydropyridinyl, dihydropyrazolyl, dihydropyrimidinyl, dihydropyrrolyl, dioxolanyl, 1,4-dithianyl, furanonyl, furanyl, imidazolidinyl, imidazolinyl, imidazolyl, imidazopyridinyl, imidazothiazolyl, indazolyl, indolinyl, indolizinyl, indolyl, isobenzotetrahydro furanyl, isobenzotetrahydrothienyl, isobenzothienyl, isochromanyl, isocoumarinyl, isoindolinyl, isoindolyl, isoquinolinyl, isothiazolidinyl, isothiazolyl, isoxazolidinyl, isoxazolyl, morpholinyl, naphthyridinyl, octahydroindolyl, octahydroisoindolyl, oxadiazolyl, oxazolidinonyl, oxazolidinyl, oxazolopyridinyl, oxazolyl, oxiranyl, perimidinyl, phenanthridinyl, phenathrolinyl, phenarsazinyl, phenazinyl, phenothiazinyl, phenoxazinyl, phthalazinyl, piperazinyl, piperidinyl, 4-piperidonyl, pteridinyl, purinyl, pyrazinyl, pyrazolidinyl, pyrazolyl, pyridazinyl, pyridinyl, pyridopyridinyl, pyrimidinyl, pyrrolidinyl, pyrrolinyl, pyrrolyl, quinazolinyl. quinolinyl, quinoxalinyl, quinuclidinyl, tetrahydrofuryl, tetrahydro furanyl, tetrahydroisoquinolinyl, tetrahydropyranyl, tetrahydrothienyl, tetrazolyl, thiadiazolopyrimidinyl, thiadiazolyl, thiamorpholinyl, thiazolidinyl, thiazolyl, thienyL triazinyl, triazolyl, and 1,3,5-trithianyl. In certain embodiments, heterocyclic may also be optionally substituted with one or more substituents Z as described herein. The term "halogen", "halide" or "halo" refers to fluorine, chlorine, bromine, and/or iodine.

The term "optionally substituted" is intended to mean that a group, including alkyl, alkenyl, alkynyl, cycloalkyl, aryl, aralkyl, heteroaryl, and heterocyclyl, may be substituted with one or more substituents Z, in one embodiment, one, two, three or four substituents Z, where each Z is independently selected from the group consisting of cyano, halo, OXO, nitro, $C_{1-6}$ alkyl, halo-$C_{1-6}$ alky!, $C_{2-6}$ alkenyl, $C_{2-6}$ alkynyl, $C_{3-7}$ cycloalkyl, $C_{6-14}$ aryl, $C_{7-14}$ aralkyl, heteroaryl, heterocyclyl, —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$. —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^f$, —NR$^e$C(O)OR$^f$, —NR$^e$C(O)NR$^f$R$^g$, —NR$^e$C(=NR$^h$)NR$^f$R$^g$, —NR$^e$S(O)R$^f$, —NR$^e$S(O)$_2$R$^f$, —NR$^e$S(O)NR$^f$R$^g$, —NR$^e$S(O)$_2$NR$^f$R$^g$, —SR$^e$, —S(O)R$^e$, and —S(O)$_2$R$^e$, and —S(O)$_2$NR$^f$R$^g$, wherein each R$^e$, R$^f$, R$^g$, and R$^h$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-14}$ aralkyl, heteroaryl, or heterocyclyl; or R$^f$ and R$^g$ together with the N atom to which they are attached form heterocyclyl.

The term "solvate" refers to a compound provided herein or a salt thereof, which further includes a stoichiometric or non-stoichiometric amount of solvent bound by non-covalent intermolecular forces. Where the solvent is water, the solvate is a hydrate.

A pharmaceutically active agent is here defined as an agent that has pharmacological, metabolic or immunological activity. This may be defined as being biologically active. This may include nutraceuticals, cosmetic agents, or pharmaceuticals.

In the sense of this disclosure, a "lipid" is any substance, which has properties like or similar to those of a fat. As a rule, it has an extended apolar group (the "chain", X) and generally also a water-soluble, polar hydrophilic part, the "head" group (Y) and has the basic Formula I:

$$X\text{-}Y_n \quad (I)$$

wherein n is equal to or larger than zero.

Lipids with n=0 are referred to as apolar lipids and lipids with n>1 are referred to as polar lipids. In this sense, all amphophilic substances, including, but not limited to glycerides, glyccrophospholipids, glycerophosphinolipids, glycerophosphonolipids, sulfolipids, sphingolipids, isoprenoid lipids, steroids or sterols and carbohydrate-containing lipids can generally be referred to as lipids, and are included as such in this disclosure. A list of relevant lipids and lipid related definitions is provided in EP 0 475 160 A1 (see, e.g. p. 4, 1. 8 to p. 6, 1. 3) and U.S. Pat. No. 6,165,500 (see, e.g., col. 6, 1. 10 to col. 7, 1. 58), each incorporated herein by reference in their entirety.

A phospholipid in various embodiments may contain (I) a moiety derived from glycerol or a sphingosine, (2) a phosphate group, and/or (3) simple organic molecule such as choline. A phospholipid as used herein may, for example, be a compound of Formula II:

wherein $R^1$ and $R^2$ are hydrogen, OH, an alkyl group, an aliphatic chain, an aliphatic chain derived from a fatty acid or a fatty alcohol: provided however that $R^1$ and $R^2$ cannot both be hydrogen, OH or a C1-C3 alkyl group; In some embodiments $R^1$ and $R^2$ are independently, an aliphatic chain, most often derived from a fatty acid or a fatty alcohol; $R^3$ generally is a hydrogen.

The OH-group of the phosphate is a hydroxyl radical or hydroxyl anion (i.e. hydroxide) form, dependent on degree of the group ionization. Furthermore, $R^4$ may be a proton or a short-chain alkyl group, substituted by a tri-short-chain alkylammonium group, such as a trimethylammonium group, or an amino-substituted short-chain alkyl group, such as 2-trimethylammonium ethyl group (cholinyl) or 2-dimethylammonium short alkyl group.

A sphingophospholipid is, for example, a compound of Formula IIB:

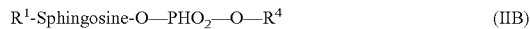

wherein $R^1$ is a fatty-acid attached via an amide bond to the nitrogen of the sphingosine and $R^4$ has the meanings given under Formula II.

A lipid preferably is a substance of formulae II or IIB, wherein $R^1$ and/or $R^2$ are acyl or alkyl, n-hydroxyacyl or n-hydroxyalkyl, but may also be branched, with one or more methyl groups attached at almost any point of the chain; usually, the methyl group is near the end of the chain (iso or anteiso). The radicals $R^1$ and $R^2$ may moreover either be saturated or unsaturated (mono-, di- or poly-unsaturated). $R^3$ is hydrogen and $R^4$ is 2-trimethylammonium ethyl (the latter corresponds to the phosphatidyl choline head group), 2-dimethylammonium ethyl, 2-methylammonium ethyl or 2-aminoethyl (corresponding to the phosphatidyl ethanolamine head group). $R^4$ may also be a proton (giving phosphatidic acid), a serine (giving phosphatidylserine), a glycerol (giving phosphatidylglycerol), an inositol (giving phosphatidylinositol), or an alkylamine group (giving phosphatidylethanolamine in case of an ethylamine), if one chooses to use a naturally occurring glycerophospholipid. Otherwise, any other sufficiently polar phosphate ester, such that will form a lipid bilayer, may be considered as well for making the compositions of the disclosure.

A phospholipid is, for example, a compound of Formula IIC as described in WO2011/022707, wherein $R^1$ and $R^2$ are independently an acyl group, alkyl group, n-hydroxyacyl group, or n-hydroxyalkyl group, most often derived from a fatty acid or a fatty alcohol, wherein $R^1$ and $R^2$ may also be branched, with one or more methyl groups attached at almost any point of the chain: usually, the methyl group is near the end of the chain (iso or anteiso). wherein $R^1$ and $R^2$ cannot both be hydrogen, OH or a $C_1$-$C_3$ alkyl group. The radicals $R^1$ and $R^2$ may moreover either be saturated or unsaturated (mono-, di- or poly-unsaturated). $R^3$ generally is a hydrogen. The OH-group of the phosphate is a hydroxyl radical or hydroxyl anion (i.e. hydroxide) form, dependent on degree of the group ionization. Furthermore. R may be a proton or a short-chain alkyl group, substituted by a tri-short-chain alkylammonium group, such as a trimethylammonium group, or an amino-substituted short-chain alkyl group, such as 2-trimethylammonium ethyl group (cholinyl) or 2-dimethylammonium short alkyl group. $R^4$ may be 2-trimethylammonium ethyl (the latter corresponds to the phosphatidyl choline head group), 2-dimethylammonium ethyl, 2-methylammonium ethyl or 2-aminoethyl (corresponding to the phosphatidyl ethanolamine head group). $R^4$ may also be a proton (giving phosphatidic acid), a serine (giving phosphatidylserine), a glycerol (giving phosphatidylglycerol), an inositol (giving phosphatidylinositol), or an alkylamine group (giving phosphatidylethanolamine in case of an ethylamine), if one chooses to use a naturally occurring glycerophospholipid. Otherwise, any other sufficiently polar phosphate ester, such that will form a lipid bilayer may be considered as well for making the compositions of the disclosure.

The table below lists preferred phospholipids in accordance with one embodiment of the disclosure.

Bechen(o)yl
Eruca(o)yl
Arachin(o)yl
Gadolen(o)yl
Arachindon(o)yl
Ole(o)yl
Stear(o)yl
Linol(o)yl
Linole(n/o)yl
Palmitole(o)yl
Palmit(o)yl
Myrist(o)yl
Laur(o)yl
Capr(o)yl The preferred lipids in the context of this disclosure are uncharged and form stable, well hydrated bilayers; phosphatidylcholines, such as soy phosphatidylcholine, phosphatidylethanolamine, and sphingomyelins are the most prominent representatives of such lipids. Any of those can have chains as listed in the table above; the ones forming fluid phase bilayers, in which lipid chains are in disordered state, being preferred.

Different negatively charged, i.e., anionic, lipids can also be incorporated into lipid bilayers of colloidal particles such as vesicles. Attractive examples of such charged lipids are phosphatidylglycerols, phosphatidylinositols and, somewhat less preferred, phosphatidic acid (and its alkyl ester) or phosphatidylserine. It will be realized by anyone skilled in the art that it is less commendable to make colloidal particles just from the charged lipids than to use them in a combination with electro-neutral bilayer component(s). In case of using charged lipids, buffer composition and/or pH care must selected so as to ensure the desired degree of lipid head-group ionization and/or the desired degree of electrostatic interaction between the, oppositely, charged drug and lipid molecules. Moreover, as with neutral lipids, the charged bilayer lipid components can in principle have any of the chains of the phospholipids as listed in the table above. The chains forming fluid phase lipid bilayers are clearly preferred, however, both due to particle adaptability increasing role of increasing fatty chain fluidity and due to better ability of lipids in fluid phase to mix with each other.

The fatty acid- or fatty alcohol-derived chain of a lipid is typically selected amongst the basic aliphatic chain types below:

| | | |
|---|---|---|
| Dodecanoic | cis-9-Tetradecanoic | 10-cis, 13-cis-Hexadecadienoic |
| Tridecanoic | cis-7-Hexadecanoic | 7-cis, 10-cis-Hexadecandienoic |
| Tetradecanoic | cis-9-Hexadecanoic | 7-cis, 10-cis, 13-cis-Hexadecatrienoic |
| Pentadecanoic | cis-9-Octadecanoic | 12-cis, 15-cis-Octadecadienoic |
| Hexadecanoic | cis-11-Octadecanoic | trans-10, trans-12-Octadecadienoic |
| Heptadecanoic | cis-11-Eicosanoic | 9-cis, 12-cis, 15-cis-Octadecatrienoic |
| Octadecanoic | cis-14-Eicosanoic | 6-cis, 9-cis,12-cis-Octadecatrienoic |
| Nonadecanoic | cis-13-Docosanoic | 9-cis, 11-trans, 13-trans-Octadecatrienoic |
| Eicosanoic | cis-15-Tetracosanoic | 8-trans, 10-trans, 12-cis-Octadecatrienoic |
| Heneicosanoic | trans-3-Hexadecanoic | 6, 9, 12, 15-Octadecatetraenoic |
| Docosanoic | tans-9-Octadecanoic | 3, 6, 9, 12-Octadecatetraenoic |
| Tricosanoic | trans-11-Octadecanoic | 3, 6, 9, 12, 15-Octadecapentaenoic |
| Tetracosanoic | | 14-cis, 17-cis-Eicosadienoic |
| | | 11-cis, 14-cis-Eicosadienoic |
| | | 8-cis, 11-cis-14-cis-Eicosadienoic |
| | | 8-cis, 11-cis-14-cis-Eicosadienoic |
| | | 5, 8, 11all-cis-Eicosatrienoic |
| | | 5, 8, 11; 14-all-cis-Eicosatrienoic |
| | | 8, 11, 14, 17-all-cis-Eicosatetraenoic |
| | | 5, 8, 11, 14, 17-all-cis-Eicosatetraenoic |
| | | 13, 16-Docosadienoic |
| | | 13, 16, 19-Docosadienoic |
| | | 10, 13, 16-Docosadienoic |
| | | 7, 10, 13, 16-Docosadienoic |
| | | 4, 7, 10, 13, 16-Docosadienoic |
| | | 4, 7, 10, 13, 16, 19-Docosadienoic |

Other double bond combinations or positions are possible as well.

Suitable fatty residues can furthermore be branched, for example, can contain a methyl group in an iso or anteiso position of the fatty acid chain, or else closer to the chain middle, as in 10-R-methyloctadecanoic acid or tuberculostearic chain Relatively important amongst branched fatty acids are also isoprenoids, many of which are derived from 3,7,11,15-tetramethylhexadec-trans-2-en-1-ol, the aliphatic alcohol moiety of chlorophyll. Examples include 5,9,13,17-tetramethyloctadecanoic acid and especially 3,7,11,15-tetramethylhexadecanoic (phytanic) and 2,6,10,14-tetramethylpentadecanoic (pristanic) acids. A good source of 4,8,12-trimethyltridecanoic acid are marine organisms. Combination of double bonds and side chains on a fatty residue are also possible.

Alternatively, suitable fatty residues may carry one or a few oxy- or cyclic groups, especially in the middle or towards the end of a chain. The most prominent amongst the later, alicyclic fatty acids, are those comprising a cyclopropane (and sometimes cyclopropene) ring, but cyclohexyl and cycloheptyl rings can also be found and might be useful for purposes of this disclosure. 2-(D)-Hydroxy fatty acids are more ubiquitous than alicyclic fatty acids, and are also important constituents of sphingolipids. Also interesting are 15-hydroxy-hexadecanoic and 17-hydroxy-octadecanoic acids, and maybe 9-hydroxy-octadeca-trans-10,trans-12-dienoic (dimorphecolic) and 13-hydroxy-octadeca-cis-9,trans-11-dienoic (coriolic) acid. Arguably the most prominent hydroxyl-fatty acid in current pharmaceutical use is ricinoleic acid, (D-(−)12-hydroxy-octadec-cis-9 enoic acid, which comprises up to 90% of castor oil, which is also often used in hydrogenated form. Epoxy-, methoxy-, and furanoid-fatty acids are of only limited practical interest in the context of this disclosure.

Generally speaking, unsaturation, branching or any other kind of derivatization of a fatty acid is best compatible with the intention of present disclosure of the site of such modification is in the middle or terminal part of a fatty acid chain. The cis-unsaturated fatty acids are also more preferable than trans-unsaturated fatty acids and the fatty radicals with fewer double bonds are preferred over those with multiple double bonds, due to oxidation sensitivity of the latter. Moreover, symmetric chain lipids are generally better suited than asymmetric chain lipids.

A preferred lipid of the Formula II is, for example, a natural phosphatidylcholine, which used to be called lecithin. It can be obtained from egg (rich in palmitic, C16:0, and oleic, C18:1, but also comprising stearic, C18:0, palmitoleic, C16:1, linolenic, C18:2, and arachidonic, C20:4 (M, radicals), soybean (rich in unsaturated C18 chains, but also containing some palmitic radical, amongst a few others), coconut (rich in saturated chains), olives (rich in monounsaturated chains), saffron (safflower) and sunflowers (rich in n-6 linoleic acid), linseed (rich in n-3 linolenic acid), from whale fat (rich in monounsaturated n-3 chains), from primrose or primula (rich in n-3 chains). Preferred, natural phosphatidyl ethanolamines (used to be called cephalins) frequently originate from egg or soybeans. Preferred sphingomyelins of biological origin are typically prepared from eggs or brain tissue. Preferred phosphatidylserines also typically originate from brain material whereas phosphatidylglycerol is preferentially extracted from bacteria, such as E. coli, or else prepared by way of transphosphatidylation, using phospholipase D, starting with a natural phosphatidylcholine. The preferably used phosphatidylinositols are isolated from commercial soybean phospholipids or bovine liver extracts. The preferred phosphatidic acid is either extracted from any of the mentioned sources or prepared using phospholipase D from a suitable phosphatidylcholine.

Furthermore, synthetic phosphatidyl cholines ($R^4$ in Formula II corresponds to 2-trimethylammonium ethyl), and $R^1$ and $R^2$ are aliphatic chains, as defined in the preceding paragraph with 12 to 30 carbon atoms, preferentially with 14 to 22 carbon atoms, and even more preferred with 16 to 20 carbon atoms, under the proviso that the chains must be chosen so as to ensure that the resulting ESAs comprise fluid lipid bilayers. This typically means use of relatively short saturated and of relatively longer unsaturated chains. Synthetic sphingomyelins ($R^4$ in Formula IIB corresponds to 2-trimethylammonium ethyl), and $R^1$ is an aliphatic chain, as defined in the preceding paragraph, with 10 to 20 carbon atoms, preferentially with 10 to 14 carbon atoms per fully saturated chain and with 16-20 carbon atoms per unsaturated chain.

Synthetic phosphatidyl ethanolamines ($R^4$ is 2-aminoethyl), synthetic phosphatidic acids ($R^4$ is a proton) or its ester ($R^4$ corresponds, for example, to a short-chain alkyl, such as methyl or ethyl), synthetic phosphatidyl serines ($R^4$ i-s L- or D-serine), or synthetic phosphatidyl (poly)alcohols, such as phosphatidyl inositol, phosphatidyl glycerol ($R^4$ is L- or D-glycerol) are preferred as lipids, wherein $R^1$ and $R^2$ are fatty residues of identical or moderately different type and length, especially such as given in the corresponding tables given before in the text. Moreover, $R^1$ can represent alkenyl and $R^2$ identical hydroxyalkyl groups, such as tetradecylhydroxy or hexadecylhydroxy, for example, in ditetradecyl or dihexadecylphosphatidyl choline or ethanolamine, $R^2$ can represent alkenyl and $R^2$ hydroxyacyl, such as a plasmalogen ($R^4$ trimethylammonium ethyl), or $R^1$ can be acyl, such as lauryl, myristoyl or palmitoyl and $R^2$ can represent hydroxy as, for example, in natural or synthetic lysophosphatidyl cholines or lysophosphatidyl glycerols or lysophosphatidyl ethanolamines, such as 1-myristoyl or 1-palmitoyllysophosphatidyl choline or -phosphatidyl ethanolamine; frequently, $R^3$ represents hydrogen.

A lipid of Formula IIB is also a suitable lipid within the sense of this disclosure. In Formula IIB, n=1, $R^1$ is an alkenyl group. $R^2$ is an acylamido group. $R^3$ is hydrogen and $R^4$ represents 2-trimethylammonium ethyl (choline group). Such a lipid is known under the name of sphingomyelin.

Suitable lipids furthermore are a lysophosphatidyl choline analog, such as 1-lauroyl-1,3-dihydroxypropane-3-phosphoryl choline, a monoglyceride, such as monoolein or monomyristin, a cerebroside, ceramide polyhexoside, sulfatide, sphingoplasmalogen, a ganglioside or a glyceride, which does not contain a free or esterified phosphoryl or phosphono or phosphino group in the 3 position. An example of such a glyceride is diacylglyceride or 1-alkenyl-1-hydroxy-2-acyl glyceride with any acyl or alkenyl groups, wherein the 3-hydroxy group is etherified by one of the carbohydrate groups named, for example, by a galactosyl group such as a monogalactosyl glycerin.

Lipids with desirable head or chain group properties can also be formed by biochemical means, for example, by means of phospholipases (such as phospholipase A1, A2, B, C and, in particular, D), desaturases, elongases, acyl transferases, etc., from natural or synthetic precursors.

Furthermore, a suitable lipid is any lipid, which is contained in biological membranes and can be extracted with the help of apolar organic solvents, such as chloroform. Aside from the lipids already mentioned, such lipids also include, for example, steroids, such as estradiol, or sterols, such as cholesterol, beta-sitosterol, desmosterol, 7-ketocholesterol or beta-cholestanol, fat-soluble vitamins, such as retinoids, vitamins, such as vitamin A1 or A2, vitamin E, vitamin K, such as vitamin K1 or K2 or vitamin DI or D3, etc.

The less soluble amphiphilic components comprise or preferably comprise a synthetic lipid, such as myristoleoyl, palmitoleoyl, petroselinyl, petroselaidyl, oleoyl, elaidyl, cis- or trans-vaccenoyl, linolyl, linolenyl, linolaidyl, octadecatetraenoyl, gondoyl, eicosaenoyl, eicosadienoyl, eicosatrienoyl, arachidoyl, cis- or trans-docosaenoyl, docosadienoyl, docosatrienoyl, docosatetraenoyl, lauroyl, tridccanoyl. myristoyl, pentadecanoyl, palmitoyl, heptadecanoyl, stearoyl or nonadecanoyl, glycerophospholipid or corresponding derivatives with branched chains or a corresponding dialkyl or sphingosin derivative, glycolipid or other diacyl or dialkyl lipid.

The more soluble amphiphilic components(s) is/are frequently derived from the less soluble components listed above and, to increase the solubility, substituted and/or complexed and/or associated with a butanoyl, pentanoyl. hexanoyl. heptanoyl, octanoyl, nonanoyl, decanoyl or undecanoyl substituent or several, mutually independent, selected substituents or with a different material for improving the solubility.

A further suitable lipid is a diacyl- or dialkyl-glycerophosphoetha-nolamine azo polyethoxylene derivative, a didecanoylphosphatidyl choline or a diacylphosphoolligomaltobionamide.

Preferably, the lipid is a phospholipid. Most preferably, the phospholipid is a phosphatidylcholine.

In some embodiments, the lipid in the composition does not comprise an alkyl-lysophospholipid. In some embodiments, the lipid in the composition does not comprise a polyeneylphosphatidylcholine.

Preferably, the amount of lipid in the composition is from about 1% to about 12%, about 1% to about 10%, about 1% to about 4%, about 4% to about 7% or about 7% to about 10% by weight.

The term "surfactant" has its usual meaning. A list of relevant surfactants and surfactant related definitions is provided in EP 0 475 160 Al (see, e.g., p. 6, 1. 5 to p. 14. 1.17) and U.S. Pat. No. 6,165,500 (see, e g., col. 7, 1. 60 to col. 19, 1. 64), each herein incorporated by reference in their entirety, and in appropriate surfactant or pharmaceutical Handbooks, such as Handbook of Industrial Surfactants or US Pharmacopoeia, Pharm. Eu. The surfactants may be those described in Tables 1-18 of U.S. Patent Application Publication No. 2002/0012680 A1. published Jan. 31, 2002, the disclosure of which is herein incorporated by reference in its entirety. The following list therefore only offers a selection, which is by no means complete or exclusive, of several surfactant classes that are particularly common or useful in conjunction with present patent application. Preferred surfactants to be used in accordance with the disclosure include those with an HLB greater than 12. The list includes ionized long-chain fatty acids or long chain fatty alcohols, long chain fatty ammonium salts, such as alkyl- or alkenoyl-trimethyl-, -dimethyl- and -methylammonium salts, alkyl- or alkenoyl-sulphate salts, long fatty chain dimethyl-aminoxides, such as alkyl- or alkenoyl-dimethyl-aminoxides, long fatty chain, for example alkanoyl, dimethyl-aminoxides and especially dodecyl dimethyl-aminoxide, long fatty chain, for example alkyl-N-methylglucamides and alkanoyl-N-methylglucamides. such as MEGA-8, MEGA-9 and MEGA-IO, N-long fatty chain-N,N-dimethylglycines, for example N-alkyl-N,N-dimethylglycines, 3-(long fatty chain-dimethylammonio)-alkane-sulphonates, for example 3-(acyidimethylammonio)-alkanesulphonatcs, long fatty chain derivatives of sulphosuccinate salts, such as bis(2-ethylalkyl) sulphosuccinate salts, long fatty chain-sulphobetaines, for example acyl-sulphobetaines, long fatty chain betaines, such as EMPIGEN BB or ZWITTERGENT-3-16, -3-14, -3-12, -3-10, or -3-8, or polyethylcn-glycol-acylphenyl ethers, especially nonaethylen-glycol-octyl-phenyl ether, polyethylene-long fatty chain-ethers, especially polyethylene-acyl ethers, such as nonaethylen-decyl ether, nonaethylen-dodecyl ether or octaethylene-dodecyl ether, polyethyleneglycol-isoacyl ethers, such as octaethyleneglycol-isotridecyl ether, polyethyleneglycol-sorbitane-long fatty chain esters, for example polyethyleneglycol-sorbitane-acyl esters and especially polyoxyethylene-monolaurate (e.g. polysorbate 20 or Tween 20), polyoxyethylene-sorbitan-monooleate (e.g. polysorbate 80 or Tween 80), polyoxyethylene-sorbitan-monolauroleylate, polyoxyethylene-sorbitan-monopetroselinate, polyoxyethylene-sorbitan-monoelaidate, polyoxyethylene-sorbitan-myristoleylate, polyoxyethylene-sorbitan-palmitoleinylate, polyoxyethylene-sorbitan-p-etroselinylate, polyhydroxyethylene-long fatty chain ethers, for example polyhydroxyethylene-acyl ethers, such as polyhydroxyethylene-lauryl ethers, polyhydroxyethylene-myristoyl ethers, polyhydroxyethylene-cetylst-earyl, polyhyd roxyethylene-palmityl ethers, polyhydroxyethylene-oleoyl ethers, polyhydroxyethylene-palmitoleoyl ethers, polyhydroxyethylene-lino-leyl, polyhydroxyethylen-4, or 6, or 8, or 10, or 12-lauryl, miristoyl, palmitoyl, palmitoleyl, oleoyl or linoeyl ethers (Brij series), or in the corresponding esters, polyhydroxyethylen-laurate, -myristate, -palmitate, -stearate or -oleate, especially polyhydroxyethylen-8-stearate (Myrj 45) and polyhydroxyethylen-8-oleate, polyethoxylated castor oil 40 (Cremophor EL), sorbitane-mono long fatty chain, for example alkylate (Arlacel or Span series), especially as sorbitane-monolaurate (Arlacel 20, Span 20), long fatty chain, for example acyl-N-methylglucamides, alkanoyl-N-methylglucamides, especially decanoyl-N-methylglucamide, dodecanoyl-N-methyl-glucamide, long fatty chain sulphates, for example alkyl-sulphates, alkyl sulphate salts, such as lauryl-sulphate (SDS), oleoyl-sulphate: long fatty chain thioglucosides, such as alkylthioglucosides and especially heptyl-, octyl- and nonyl-beta-D-thioglucopyranoside; long fatty chain derivatives of various carbohydrates, such as pentoses, hcxoses and disaccharidcs, especially alkyl-glucosides and maltosides, such as hexyl-, heptyl-, octyl-, nonyl- and decyl-beta-D-glucopyranoside or D-maltopyranosidc; further a salt, especially a sodium salt, of cholate, deoxycholate, glycocholate, glycodcoxycholate, taurodeoxycholate, taurocholate, a fatty acid salt, especially oleate, elaidate, linoleate, laurate, or myristate, most often in sodium form, lysophospholipids, n-octadecylene-glycerophosphatidic acid, octadecylene-phosphorylglycerol, octadecylene-phosphorylserine, n-long fatty chain-glycero-phosphatidic acids, such as n-acyl-glycero-phosphatidic acids, especially lauryl glycero-phosphatidic acids, oleoyl-glycero-phosphatidic acid, n-long fatty chain-phosphoryl glycerol, such as n-acyl-phosphorylglycerol, especially lauryl-, myristoyl-, oleoyl- or palmitoeloyl-phosphorylglycerol, n-long fatty chain-phosphorylserine, such as n-acyl-phosphorylserine, especially lauryl-, myristoyl-, oleoyl- or palmitoeloyl-phosphorylserine, n-tetradecyl-glycero-phosphatidic acid, n-tetradecyl-phosphorylglycerol, n-tetradecyl-phosphoryl-serine, corresponding-, elaidoyl-, vaccenyl-lysophospholipids, corresponding short-chain phospholipids, as well as all surface active and thus membrane destabilising polypeptides. Surfactant chains are typically chosen to be in a fluid state or at least to be compatible with the maintenance of fluid-chain state in carrier aggregates.

The surfactant may be present in the composition in about 0.2 to 10%, about 1% to about 10%, about 1% to about 7% or about 2% to 5% by weight.

Preferably, the surfactant is a nonionic surfactant.

The nonionic surfactant may be selected from the group consisting of: polyoxyethylene sorbitans (polysorbate surfactants), polyhydroxyethylene stearates or polyhydroxyethylene laurylethers (Brij surfactants). Preferably, the surfactant is a polyoxyethylene-sorbitan-monooleate (e.g. polysorbate 80 or Tween 80) or Tween 20, 40 or 60. The polysorbate may have any chain with 12 to 20 carbon atoms. The polysorbate may be fluid in the composition, which may contain one or more double bonds, branching, or cyclo-groups.

The compositions of the invention may comprise only one lipid and only one surfactant. Alternatively, the compositions of the invention may comprise more than one lipid and only one surfactant, e.g., two, three, four, or more lipids and one surfactant. The compositions of the invention may also comprise only one lipid and more than one surfactant, e.g., two, three, four, or more surfactants and one lipid. The compositions of the invention may also comprise more than one lipid and more than one surfactant, e.g., two, three, four, or more lipids and two, three, four, or more surfactants.

The compositions of the invention may have a range of lipid/phospholipid to surfactant ratios. The ratios may be expressed in terms of molar terms (mol lipid/mol surfactant or mol phospholipid/mol surfactant). The molar ratio of lipid or phospholipid to surfactant in the compositions may be from about 1:3 to about 30:1, from about 1:2 to about 30:1, from about 1:1 to about 30:1, from about 2:1 to about 20:1, from about 5:1 to about 30:1, from about 10:1 to about 30:1, from about 15:1 to about 30:1, or from about 20:1 to about 30:1. The molar ratio of lipid or phospholipid to surfactant in the compositions of the invention may be from about 1:2 to about 10:1. The ratio may be from about 1:1 to about 2:1, from about 2:1 to about 3:1, from about 3:1 to about 4:1. from about 4:1 to about 5:1 or from about 5:1 to about 10:1. The molar ratio may be from about 10.1 to about 30:1, from about 10:1 to about 20:1, from about 10:1 to about 25:1, and from about 20:1 to about 25:1. The lipid or phospholipid to surfactant ratio may be about 1.0:1.0, about 1.25:1.0, about 1.5/1.0, about 1.75/1.0, about 2.0/1.0, about 2.5/1.0, about 3.0/1.0 or about 4.0/1.0. Preferably, all of the deformable colloidal particles in a composition of the present invention have the same lipid or phospholipid to surfactant ratio.

The compositions of the invention may also have varying amounts of total amount of the following components: lipid or phospholipid and surfactant combined (TA). The TA amount may be stated in terms of weight percent of the total composition. Preferably, the TA is from about 1% to about 40%, about 5% to about 30%, about 7.5% to about 15%, about 6% to about 14%, about 8% to about 12%, about 5% to about 10%, about 10% to about 20% or about 20% to about 30%. More preferably, the TA is 6%, 8%, 9%, 10%, 15% or 20%.

Selected ranges for total lipid/phospholipid amounts and lipid/surfactant or phospholipid/surfactant ratios (mol/mol) for the compositions of the invention are described in the Table below:

| Total Amount and Lipid/Phospholipid to Surfactant Ratios | |
| --- | --- |
| TA (%) | Lipid/Surfactant or Phospholipid/ Surfactant (mol/mol) |
| 5 to 10 | 1.0 to 1.25 |
| 5 to 10 | 1.25 to 1.72 |
| 5 to 10 | 1.75 to 2.25 |
| 5 to 10 | 2.25 to 3.00 |
| 5 to 10 | 3.00 to 4.00 |
| 5 to 10 | 4.00 to 8.00 |
| 5 to 10 | 10.00 to 13.00 |

-continued

Total Amount and Lipid/Phospholipid to Surfactant Ratios

| TA (%) | Lipid/Surfactant or Phospholipid/Surfactant (mol/mol) |
|---|---|
| 5 to 10 | 15.00 to 20.00 |
| 5 to 10 | 20.00 to 22.00 |
| 5 to 10 | 22.00 to 25.00 |
| 10 to 20 | 1.0 to 1.25 |
| 10 to 20 | 1.25 to 1.75 |
| 10 to 20 | 1.25 to 1.75 |
| 10 to 20 | 2.25 to 3.00 |
| 10 to 20 | 3.00 to 4.00 |
| 10 to 20 | 4.00 to 8.00 |
| 10 to 20 | 10.00 to 13.00 |
| 10 to 20 | 15.00 to 20.00 |
| 10 to 20 | 20.00 to 22.00 |
| 10 to 20 | 22.00 to 25.00 |

The compositions of the invention may optionally contain one or more of the following ingredients: co-solvents, chelators, buffers, pH adjuster, antioxidants, preservatives, microbicides, antimicrobials, emollients, humectants, lubricants co-solvents, thickeners and fragrances. Preferably, these other components of the composition are not associated with the colloidal particles of the present invention. Preferred amounts of optional components are described as follows.

| | Molar (M) or | Rel w %* |
|---|---|---|
| Antioxidant: | | |
| Primary: | | |
| Butylated hydroxyanisole, BHA | | 0.1-8 |
| Butylated hydroxytoluene BHT | | 0.1-4 |
| Thymol | | 0.1-1 |
| Metabisulphite | 1-5 mM | |
| Bisulphite | 1-5 mM | |
| Thiourea (MW = 76.12) | 1-10 mM | |
| Monothioglycerol (MW = 108.16) | 1-20 mM | |
| Propyl gallate (MW = 212.2) | | 0.02-0.2 |
| Ascorbate (MW = 175.3+ ion) | 1-10 mM | |
| Palmityl-ascorbate | | 0.01-1 |
| Tocopherol-PEG | | 0.5-5 |
| Secondary (chelator) | | |
| EDTA (MW = 292) | 1-10 mM | |
| EGTA (MW = 380.35) | 1-10 mM | |
| Desferal (MW = 656.79) | 0.1-5 mM | |
| Buffer | | |
| Acetate | 30-150 mM | |
| Phosphate | 10-50 mM | |
| Triethanolamine | 30-150 mM | |

*as a percentage of total lipid quantity

The compositions of the invention may include a buffer to adjust the pH of the aqueous solution. Preferably, the aqueous solution has a pH in the range pH 3.5 to pH 9, pH 4 to pH 7.5, or pH 6 to pH 7. Examples of buffers include, but are not limited to acetate buffers, lactate buffers, phosphate buffers, and propionate buffers. Preferably, the compositions comprise one or more buffers selected from the group consisting of disodium hydrogen orthophosphate dodecahydrate, disodium hydrogen orthophosphate anhydrous, sodium dihydrogen orthophosphate dehydrate, sodium dihydrogen orthophosphate dodecahydrate and phosphate buffer, for example phosphate (pH6.7) buffer.

A particularly preferred pH adjuster is sodium hydroxide.

The compositions of the invention are preferably formulated in aqueous media. The compositions may be formulated with or without co-solvents, such as lower alcohols. The compositions of the invention may comprise at least 20% by weight water. The compositions of the invention may comprise about 20%, about 30%, about 40%, about 50%, about 60% about 70%, about 80%, about 90% by weight water. The composition may comprise from about 70% to about 80% by weight water. Preferably, the compositions comprise one or more solvents selected from the group consisting of purified water, ethanol, for example ethanol (96%), benzyl alcohol and paraben.

A "microbicide" or "antimicrobial'" agent is commonly added to reduce the bacterial count in pharmaceutical compositions. Some examples of microbicides are short chain alcohols, including ethyl and isopropyl alcohol, chlorbutanol, benzyl alcohol, chlorbenzyl alcohol, dichlorbenzylalcohol, hexachlorophene; phenolic compounds, such as cresol, 4-chloro-m-cresol, p-chloro-m-xylenol. dichlorophene, hexachlorophene, povidon-iodine; parabenes. especially alkylparabenes, such as methyl-, ethyl-, propyl-, or butyl-paraben, benzyl paraben; acids, such as sorbic acid, benzoic acid and their salts; quaternary ammonium compounds, such as alkonium salts, e.g., a bromide, benzalkonium salts, such as a chloride or a bromide, cetrimonium salts, e.g., a bromide, phenoalkecinium salts, such as phenododecinium bromide, cetylpyridinium chloride and other salts; furthermore, mercurial compounds, such as phenylmercuric acetate, borate, or nitrate, thiomersal, chlorhexidine or its gluconate, or any antibiotically active compounds of biological origin, or any suitable mixture thereof. Preferably, the compositions comprise one or more preservative selected from the group consisting of methyl paraben and ethyl paraben.

Examples of "antioxidants" are butylhydroxyanisole or butylated hydroxyanisol (BHA), butylated hydroxytoluene (BHT) and di-tert-butylphenol (LY178002, LY256548, HWA-131, BF-389, 01-986, PD-127443, E-51 or 19, BI-L-239XX, etc.), tertiary butylhydroquinone (TBHQ), propyl gallate (PG), I-O-hexyl-2,3,5-trimethylhydroquinone (HTHQ); aromatic amines (diphenylamine, p-alkylthio-o-anisidine, ethylenediamine derivatives, carbazol, tetrahydroindenoindol); phenols and phenolic acids (guaiacol, hydroquinone, vanillin, gallic acids and their esters, protocatechuic acid, quinic acid, syringic acid, ellagic acid, salicylic acid, nordihydroguaiaretic acid (NDGA), eugenol); tocopherols (including tocopherols (alpha, beta, gamma, delta) and their derivatives, such as tocopheryl-acylate (e g. -acetate.-laurate. myristate, -palmitate, -oleate, -linoleate. etc., or an y other suitable tocopheryl-lipoate). tocopheryl-POE-succinate; trolox and corresponding amide and thiocarboxamide analogues; ascorbic acid and its salts, isoascorbate, (2 or 3 or 6)-o-alkylascorbic acids, ascorbyl esters (e.g., 6-o-lauroyl, myristoyl, palmitoyl-, oleoyl, or linoleoyl-L-ascorbic acid, etc.). Also useful are the preferentially oxidised compounds, such as sodium bisulphite, sodium metabisulphite, thiourea; chellating agents, such as EDTA, GDTA, desferral: miscellaneous endogenous defence systems, such as transferrin, lactoferrin, ferritin, cearuloplasmin, haptoglobion, heamopexin, albumin, glucose, ubiquinol-10); enzymatic antioxidants, such as superoxide dismutase and metal complexes with a similar activity, including catalase, glutathione peroxidase, and less complex molecules, such as beta-carotene, bilirubin, uric acid; flavonoids (flavones, flavonols, flavonones, flavanonals, chacones, anthocyanins). N-acetylcystein, mesna. glutathione, thiohistidine derivatives, triazoles; tannines, cinnamic acid, hydroxycinnamatic acids and their esters (coumaric acids and esters, caffeic acid and their esters, ferulic acid, (iso-) chlorogenic acid, sinapic acid); spice extracts (e.g., from clove, cinnamon, sage, rosemary, mace, oregano, allspice, nutmeg); carnosic acid, carnosol, carsolic acid; rosmarinic acid, rosmaridiphenol, gentisic acid, ferulic acid; oat flour extracts, such as avenanthramide 1 and 2; thioethers, dithioethers, sulphoxides, tetralkylthiuram disulphides; phytic acid, steroid derivatives (e.g., U74006F); tryptophan metabolites (e.g., 3-hydroxykynurenine, 3-hydroxyanthranilic acid), and organochalcogenides. Preferably, the compositions comprise one or more antioxidants selected from the group consisting of butylated hydroxyanisol (BHA), butylated hydroxytoluene (BHT) and sodium metabisulphate.

Particularly preferred chelating agents are EDTA and disodium edetate.

"Thickeners" are used to increase the viscosity of pharmaceutical compositions to and may be selected from selected from pharmaceutically acceptable hydrophilic polymers, such as partially etherified cellulose derivatives, comprising carboxymethyl-, hydroxyethyl-, hydroxypropyl-, hydroxypropylmethyl- or methyl-cellulose; hydroxypropyl ethylcellulose, microcrystalline cellulose, completely synthetic hydrophilic polymers comprising polyacrylates, polymethacrylates, poly(hydroxyethyl)-, poly(hydroxypropyl)-, poly(hydroxypropylmethyl)methacrylate, polyacrylonitrile, methallyl-sulphonate, polyethylenes, polyoxiethylenes, polyethylene glycols, polyethylene glycol-lactide, polyethylene glycol-diacrylate, polyvinyl pyrrolidone, polyvinyl alcohols, poly(propylmethacrylamide), poly(propylene fumarate-co-ethylene glycol), poloxamers, polyaspartamide, (hydrazine cross-linked) hyaluronic acid, silicone; cellulose gum, natural gums comprising alginates, carrageenan, *Ceratonia siliqua* gum, guar-gum, gelatine, gellan, tragacanth, (amidated) pectin, xanthan, chitosan collagen, agarose; a mixture of glyceryl acrylate and acrylic acid, chitosan, mixtures and further derivatives or co-polymers thereof and/or other pharmaceutically, or at least biologically, acceptable polymers. Preferably, the compositions comprise a carbomer such as carbopol, for example carbopol 974P NF, as a thickener.

A particularly preferred humectant is glycerol.

A particularly preferred fragrance is linalool.

The compositions of the present invention may also comprise a polar liquid medium. The compositions of the present invention may be administered in an aqueous medium.

The compositions of the present invention may comprise menthol. This is particularly preferred when the AOI comprises capsaicin. The composition may comprise 0.05 to 1% menthol by weight, more preferably 0.05 to 0.5% menthol by weight, most preferably approximately 0.1% menthol by weight. The menthol may be incorporated into the membrane of the deformable colloidal particle.

The compositions of the invention may comprise one or more additional Agents of Interest (AOI). As discussed above, these additional AOIs may be associated with the deformable colloidal particles.

Preferably, any additional AOIs are not associated with the deformable colloidal particles. These additional AOIs may be selected from the group consisting of an antiseptic, an antibiotic, an anaesthetic, an analgesic, a skin lightener, and antihistamine, a steroid, an anti-inflammatory agent, an anti-viral, sun block, moisturizer, nicotine, anti-fungal, antimicrobial, nutraceuticals, an essential oil and a hormone.

These additional AOIs may be present within the continuous phase of the composition, for example dissolved in the medium of suspension, or within a different dispersed phase of the composition, for example in the form of an insoluble aggregate or associated with non-deformable colloidal particles such as micelles and non-deformable vesicles such as liposomes.

One particularly preferred composition of the present invention comprises insoluble aggregates or micelles of chlorhexidine or a salt thereof, preferably chlorhexidine digluconate, together with empty deformable colloidal particles, preferably Sequessomes™, and deformable colloidal particles, preferably Tethersomes, to which zinc stearate has been tethered.

A second particularly preferred composition of the present invention comprises insoluble aggregates of capsaicin together with deformable colloidal particles, preferably Transfersomes™ the membranes of which comprise menthol.

A third particularly preferred composition of the present invention comprises liposomes comprising capsaicin, menthol and phospholipids together with deformable colloidal particles, preferably Transfersomes™, the membranes of which comprise menthol.

A fourth particularly preferred composition of the present invention comprises insoluble aggregates of capsaicin together with empty deformable colloidal particles, preferably Sequessomes™.

A fifth particularly preferred composition comprises myristyl salicylate or tridecyl salicylate dissolved in the continuous phase, and deformable colloidal particles, preferably Tethersomes, to which myristyl salicylate or tridecyl salicylate are tethered. Preferably, tocopherol is present in the composition in a separate phase. This composition may additionally comprise a second type of deformable colloidal particle, preferably Tethersomes, to which palmitoyl ascorbic acid and tocopheryl linoleate are tethered.

A sixth particularly preferred composition comprises glucosamine hydrochloride and chondroitin sulphate dissolved in the continuous phase, and deformable colloidal particles, preferably Tethersomes, to which palmitoyl ascorbate and tocophenyl linoleate are preferably tethered. One embodiment of such a composition is set out in Example 4.

A seventh particularly preferred composition comprises N-acetyl glucosamine sulphate and chondroitin sulphate dissolved in the continuous phase, and deformable colloidal particles, preferably Tethersomes, to which palmitoyl ascorbic acid and tocopheryl linoleate are preferably tethered. One embodiment of such a composition is set out in Example 4.

An eighth particularly preferred composition comprises caffeine dissolved in the continuous phase, and deformable colloidal particles, preferably Tethersomes, to which palmitoyl ascorbic acid is preferably tethered. Preferably, this composition additionally comprises two further types of deformable colloidal particles, a first to which palmitoyl tripeptide-1 is tethered and a second to which palmitoyl tetrapeptide-7 is tethered. Both of these deformable colloidal particles preferably also comprise Tethersomes. Preferably, the composition comprises tocopherol as a separate phase. One embodiment of such a composition is set out in Example 5.

A ninth particularly preferred composition comprises tocopherol in the continuous phase and salicylic acid or a salt or ester thereof, preferably myristyl salicylate or tridecyl salicylate, tethered to the deformable colloidal particles, preferably Tethersomes. Preferably, this composition additionally comprises a further type of deformable colloidal particle, preferably Tethersomes, to which palmityol ascorbic acid and tocopheryl linoleate are tethered.

A tenth particularly preferred composition of the present invention comprises an AOI in combination with soy phosphatidylcholine, polysorbate 80 and one or more of butylhydroxyanisole, ethanol, zinc stearate, methyl-4-hydroxybenzoate (methyl paraben), ethyl-4-hydroxybenzoate (ethyl paraben), benzylalcohol, citric acid monohydrate, di-sodium hydrogen orthophosphate anhydrous, sodium hydroxide, carbopol 974P, glycerol and water. Preferably, the AOI is chlorhexidine digluconate which may be present in the composition as micelles. Preferably, the zinc stearate, where present, is tethered to the colloidal particles which have a membrane mainly comprising soy phosphatidylcholine and polysorbate 80.

An eleventh particularly preferred composition of the present invention comprises a AOI in combination with soy phosphatidylcholine, polysorbate 80 and one or more of butylhydroxytoluene, ethanol, methyl-4-hydroxybenzoate, ethyl-4-hydroxybenzoate, benzylalchohol, sodium dihydrogen orthophosphate dihydrate, di-sodium hydrogen orthophosphate dodecahydrate, sodium hydroxide, carbophol 974P, glycerol and water. Preferably, the AOI is capsaicin. The capsaisin may be present in the composition as insoluble aggregates which are not associated with the colloidal particles which have a membrane mainly comprising soy phosphatidylcholine and polysorbate 80.

An twelfth particularly preferred composition of the present invention comprises the same composition as the eleventh particularly preferred composition, above, with the addition of menthol. Preferably, the menthol is associated with the colloidal particles.

A thirteenth particularly preferred composition of the present invention comprises an AOI in combination with soy phosphatidylcholine, polysorbate 80 and one or more of butylhydroxyanisole (BHA), ethanol, methyl-4-hydroxybenzoate, ethyl-4-hydroxybenzoate, benzylalchohol, di-sodium hydrogen orthophosphate dodecahydrate, sodium hydroxide, carbophol 974P, glycerol and water. Preferably, the AOI is glucosamine hydrochloride or N-acetyl glucosamine sulphate in combination with chondroitin sulphate. Preferably, these AOI are dissolved in the continuous phase and are not associated with the colloidal particles which have a membrane mainly comprising soy phosphatidylcholine and polysorbate 80. Preferably, palmitoyl ascorbate and tocophenyl linoleate are tethered to the deformable colloidal particles.

A fourteenth particularly preferred composition of the present invention comprises an AOI in combination with soy phosphatidylcholine, polysorbate 80 and one or more of butylhydroxyanisole (BHA), ethanol, methyl-4-hydroxybenzoate, ethyl-4-hydroxybenzoate, benzylalchohol, di-sodium hydrogen orthophosphate dodecahydrate, sodium hydroxide, carbophol 974P, glycerol and water. Preferably, the AOI is caffeine dissolved in the continuous phase and is not associated with the colloidal particles which have a membrane mainly comprising soy phosphatidylcholine and polysorbate 80. Preferably, palmitoyl ascorbic acid is tethered to the deformable colloidal particles. Preferably, the composition additionally comprises tocopherol as a separate phase.

A fifteenth particularly preferred composition of the present invention comprises an AOI in combination with soy phosphatidylcholine, polysorbate 80 and one or more of butylhydroxyanisole (BHA), ethanol, methyl-4-hydroxybenzoate, ethyl-4-hydroxybenzoate, benzylalchohol, di-sodium hydrogen orthophosphate dodecahydrate, sodium hydroxide, carbophol 974P, glycerol and water. Preferably, the AOIs are tocopherol in the continuous phase and salicylic acid or a salt of ester thereof, preferably myristyl salicylate or tridecyl salicylate, tethered to deformable colloidal particles which have a membrane mainly comprising soy phosphatidylcholine and polysorbate 80. Preferably, the composition additionally comprises a further type of deformable colloidal particle, which has a membrane mainly comprising soy phosphatidylcholine and polysorbate 80, to which palmityol ascorbic acid and tocopheryl linoleate are tethered.

The invention is described below with reference to the following examples and figures in which:

EXAMPLE 1: METHOD OF MANUFACTURE

Figure 1:
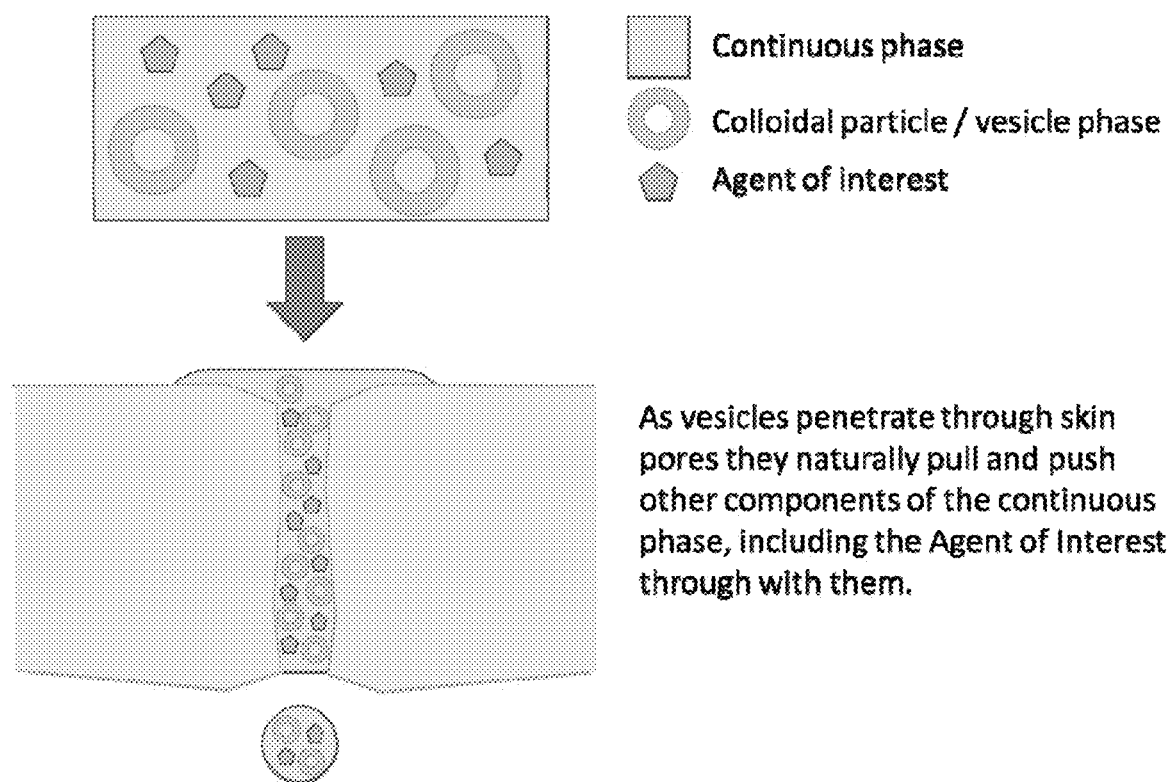
FIG. 1 is a diagram of the movement of the deformable colloidal particles and AOI of the compositions of the present invention through the skin.
Figure 2:
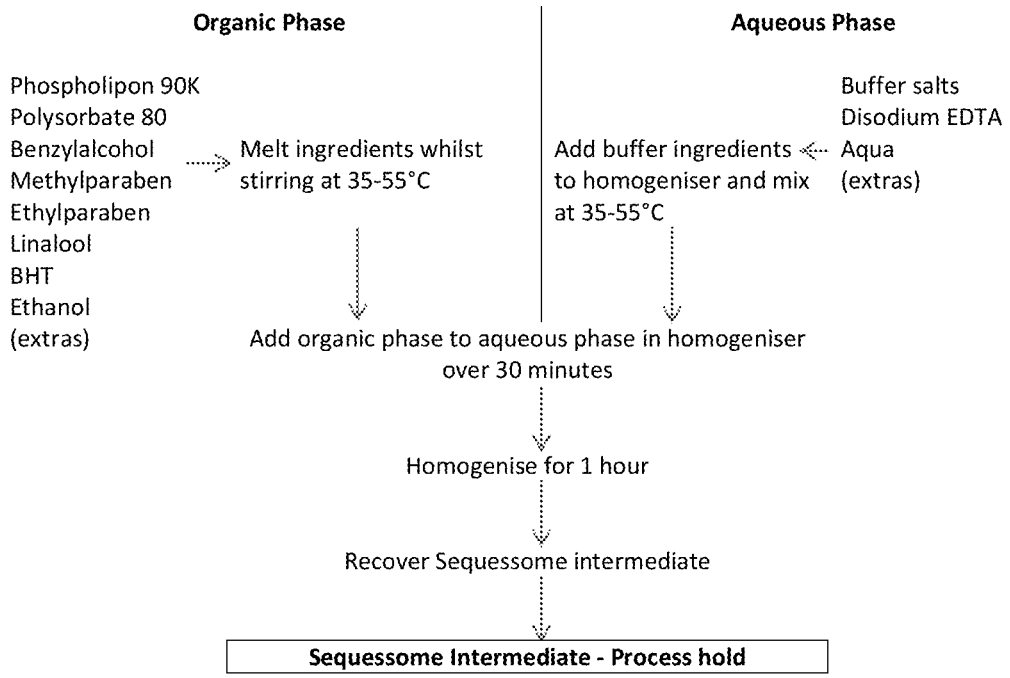
FIG. 2 shows a simplified generic manufacturing process for compositions of the present invention.
Figure 2:
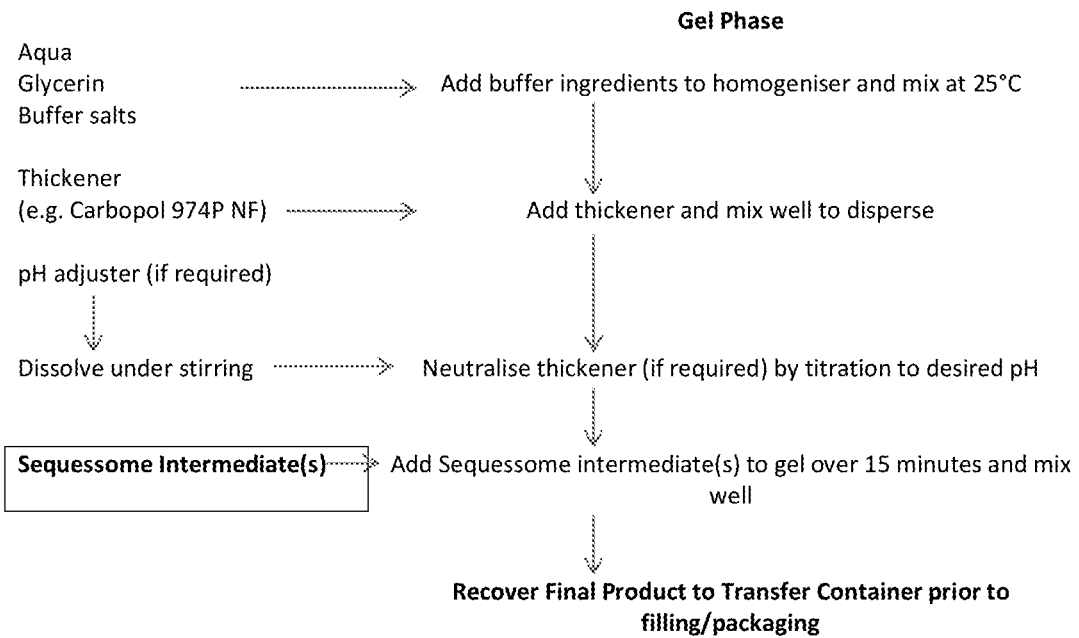

A simplified generic manufacturing process of compositions in accordance with the present invention is illustrated in FIG. 2 and can be summarised as follows. Firstly, the colloidal dispersion comprising the deformable colloidal particles (for example, the Sequessome™ intermediate) is made. This colloidal dispersion is formed from an 'organic phase' containing alcohol-soluble components and an 'aqueous phase' consisting of water-soluble components. Secondly, the gel phase (a thickener) is formed within which the colloidal dispersion is dispersed. During this secondary stage, more than one kind of colloidal dispersion may be introduced such that the final composition comprises more than one kind of colloidal particle. During secondary manufacture, the AOI is added to the gel phase.

EXAMPLE 2: AN IN-USE STUDY IN HEALTHY VOLUNTEERS TO INVESTIGATE THE ANTI-SPOT EFFICACY OF TWO TEST ARTICLES COMPRISING CHLORHEXIDINE, USING OBJECTIVE INSTRUMENTAL ASSESSMENTS OF SKIN SEBUM LEVELS AND SUBJECTIVE VISUAL ASSESSMENTS OF LESION PREVALENCE, AGAINST A PLACEBO FOLLOWING A 3-WEEK USE PERIOD

Summary

This study compared two variants of a multiphasic Sequessome™-based mixed product with a control product in their ability to control sebum and reduce the incidence of acne in acne-prone individuals.

The test products (n=36 and n=37) contained two types of deformable colloidal particle, namely Sequessomes™

(empty SPC/Tween (polysorbate) vesicles) and Tethersomes comprising tethered zinc, in addition to other excipients, including chlorhexidine as an anti-microbial. The Sequessomes™ and Tethersomes in the two products contained different ratios of SPC:Tween (polysorbate) to assess if this affected the efficacy of the product. The control product contained no vesicles, zinc or chlorhexidine (n=20).

The objectively measured results demonstrated that against the control product the test products:

Significantly reduced surface sebum (by up to 50%)[1]

[1] Published data demonstrate that a reduction in sebum production of 30-50% correlates with reduced acne symptoms (Janiczek-Dolphin N1, Cook J, Thiboutot D, Harness J, Clucas A: *Can sebum reduction predict acne outcome?* Br J Dermatol. 2010 October; 163(4):683-8)

Significantly reduced comedones

Significantly reduced the numbers of papules and pustules

TABLE 1

Summary of results

| Objective assessment | Test Article 1 | Test Article 2 |
|---|---|---|
| Reduction in sebum after... | 1 week >20%; 3 weeks >50% | 1 week >20%; 3 weeks >50% |
| Reduction in comedones after... | 1 week >40%; 3 weeks >90% | 1 week = 50%; 3 weeks >80% |
| Reduction in pustules after... | 1 week = 90%; 3 weeks >98% | 1 week >90%; 3 weeks >98% |
| Subjective assessment: % agreeing/strongly agreeing | | |
| Product reduced blackheads | 64.7% | 76.5% |
| Product stopped spots recurring | 69.6% | 74.5% |
| Spots less painful (tender to touch) | 66.7% | 82.4% |
| Spots not as swollen | 73.5% | 75.5% |
| Skin less shinySkin less oily | 59.8% | 80.4% |
| Skin less greasy | 67.6% | 77.5% |
| | 69.6% | 75.5% |

The results showed the multifunctional nature of the product. We hypothesise that the Sequessomes™ both assisted in the clearing of the excess sebum from the skin surface, whilst their penetration into the skin dragged the chlorhexidine in solution into the skin structure, killing bacteria. The tethered zinc may also have had a role in both reducing sebum production and/or having an anti-microbial function.

The test articles were both well tolerated with no adverse effects (AEs) reported and no erythema at the test site.

These results demonstrate that the test compositions are a very effective treatment for acne. The reduction in sebum and both spots and blackheads by 21 days supports the role of these compositions in preventing future recurrences of the symptoms of acne.

Methods
Summary Protocol

| Study design: | Single-blind, within-subject comparison. |
|---|---|
| Test Groups: | Test article 1. CBL-DERM-14-005-E Test Article 2. CBL-DERM-14-006-F Control: CBL-DERM-14-008-P |
| Dose regime: | The test groups followed a 12-week usage schedule according to treatment specific in-use regimes. |
| Duration of study: | 21 Days. |
| Number of subjects: | 36 subjects completed the active phase for group 1, 37 subjects for group 2 and 20 subjects completed assessments for group 3. |
| Study design: | Single-blind, within-subject comparison. |
| Duration of study: | Study Started: w/c 26 Jan. 2015 |
| Study Ended: | w/e 20 Feb. 2015 |
| Location: | Princeton Consumer Research Ltd. 307 College Road East Princeton New Jersey 08540 |

Test Articles—Summary Formulae:
Quantities required per 100 g final product:

| | CBL-DERM-14-006-F | CBL-DERM-14-005-E | CBL-DERM-14-008-P |
|---|---|---|---|
| SPC (dry mass) | 6.870 g | 7.146 g | |
| Polysorbate 80 | 0.850 g | 0.472 g | |
| Benzylalcohol | 0.525 g | 0.525 g | |
| Methyl-4-hydroxybenzoate | 0.250 g | 0.250 g | 0.250 g |
| Ethyl-4-hydroxybenzoate | 0.250 g | 0.250 g | 0.250 g |
| Butylhydroxyanisol | 0.020 g | 0.020 g | |
| Linalool | 0.100 g | 0.100 g | |
| Disodium hydrogen phosphate 12 $H_2O$ | 0.530 g | 0.530 g | 0.530 g |
| Citric acid monohydrate | 0.128 g | 0.128 g | 0.128 g |
| Glycerol | 3.000 g | 3.000 g | |
| Ethanol | 3.569 g | 3.418 g | |
| Sodium hydroxide | 0.113 g | 0.113 g | 0.150 g |
| Carbopol 947P NF | 0.750 g | 0.750 g | 1.000 g |
| Water | 81.463 g | 81.716 g | 97.692 g |
| Agent of Interest-present in continuous phase | | | |
| Chlorhexidine digluconate (20% solution)** | 1.500 g | 1.500 g | |
| Agent of Interest-tethered to Tethersomes | | | |
| Zinc Stearate | 0.082 g | 0.082 g | |
| pH | 5.5 | 5.5 | 5.5 |

**% with respect to the salt

Test Articles—Detailed Formulation Information:
CBL-DERM-14-006-F:

| Organic Phase-Empty Sequessome Intermediate | Quantity Required Per 100 g Final Product (g) |
|---|---|
| SPC | 3.43500 |
| Ethanol | 1.82550 |
| BHA | 0.01000 |
| Methyl-4-hydroxybenzoate | 0.12500 |
| Ethyl-4-hydroxybenzoate | 0.12500 |
| Benzyl alcohol | 0.26250 |
| Polysorbate 80 | 0.42500 |
| Linalool | 0.05000 |
| Organic Phase Sub-Total | 6.25800 |
| Aqueous Phase-Empty Sequessome Intermediate | |
| Citric acid monohydrate | 0.03600 |
| diNa hydrogen phos 12 H20 | 0.14400 |
| Water | 22.72850 |
| Aqueous Phase Sub-Total | 22.90850 |
| Empty Sequessome Intermediate Total | 29.16650 |
| Organic Phase-Zinc Stearate Intermediate | |
| SPC | 3.43500 |
| Ethanol | 1.74350 |
| BHA | 0.01000 |
| Methyl-4-hydroxybenzoate | 0.12500 |
| Ethyl-4-hydroxybenzoate | 0.12500 |
| Benzyl alcohol | 0.26250 |

-continued

| Organic Phase-Empty Sequessome Intermediate | Quantity Required Per 100 g Final Product (g) |
|---|---|
| Polysorbate 80 | 0.42500 |
| Zinc stearate | 0.08200 |
| Linalool | 0.05000 |
| Organic Phase Sub-Total | 6.25800 |
| Aqueous Phase-Zinc Stearate Intermediate | |
| Citric acid monohydrate | 0.03600 |
| diNa hydrogen phos 12 H20 | 0.14400 |
| Water | 22.72850 |
| Aqueous Phase Sub-Total | 22.90850 |
| Zinc Tethersomes Intermediate Total | 29.16650 |
| Sum of Sequessome and Tethersome Intermediates | 58.33300 |
| Gel Phase-Final Product | |
| Citric acid monohydrate | 0.05600 |
| diNa hydrogen phos 12 H20 | 0.24200 |
| Sodium hydroxide | 0.11300 |
| Carbopol 974P | 0.75000 |
| Glycerol | 3.00000 |
| Water | 36.00600 |
| Gel Phase Sub-Total | 40.16700 |
| Chlorhexidine digluconate | 1.50000 |
| Overall Total | 100.00000 |

CBL-DERM-14-005-E:

| Organic Phase-Empty Sequessome Intermediate | Quantity Required Per 100 g Final Product (g) |
|---|---|
| SPC | 3.57300 |
| Ethanol | 1.75000 |
| BHA | 0.01000 |
| Methyl-4-hydroxybenzoate | 0.12500 |
| Ethyl-4-hydroxybenzoate | 0.12500 |
| Benzyl alcohol | 0.26250 |
| Polysorbate 80 | 0.23600 |
| Linalool | 0.05000 |
| Organic Phase Sub-Total | 6.13150 |

-continued

| Organic Phase-Empty Sequessome Intermediate | Quantity Required Per 100 g Final Product (g) |
|---|---|
| Aqueous Phase-Empty Sequessome Intermediate | |
| Citric acid monohydrate | 0.06400 |
| diNa hydrogen phos 12 H20 | 0.26500 |
| Water | 34.30000 |
| Aqueous Phase Sub-Total | 34.62900 |
| Empty Sequessome Intermediate Total | 40.76050 |
| Organic Phase-Zinc Stearate Intermediate | |
| SPC | 3.57300 |
| Ethanol | 1.66800 |
| BHA | 0.01000 |
| Methyl-4-hydroxybenzoate | 0.12500 |
| Ethyl-4-hydroxybenzoate | 0.12500 |
| Benzyl alcohol | 0.26250 |
| Polysorbate 80 | 0.23600 |
| Zinc stearate | 0.08200 |
| Linalool | 0.05000 |
| Organic Phase Sub-Total | 6.13150 |
| Aqueous Phase-Zinc Stearate Intermediate | |
| Citric acid monohydrate | 0.06400 |
| diNa hydrogen phos 12 H20 | 0.26500 |
| Water | 34.30000 |
| Aqueous Phase Sub-Total | 34.62900 |
| Zinc Tethersome Intermediate Total | 40.76050 |
| Sum of Sequessome and Tethersome Intermediates | 81.52100 |
| Gel Phase-Final Product | |
| Sodium hydroxide | 0.11300 |
| Carbopol 974P | 0.75000 |
| Glycerol | 3.00000 |
| Water | 13.11600 |
| Gel Phase Sub-Total | 16.97900 |
| Chlorhexidine digluconate | 1.50000 |
| Overall Total | 100.00000 |

Results

1. Sebum Reduction

TABLE 2

Average reduction in Sebum score from Day 0. A negative score indicates an increase in sebum.

| | | n | Day 3 | Day 7 | Day 14 | Day 21 |
|---|---|---|---|---|---|---|
| Test article 1 | | 36 | 20.47 | 34.94 | 71.64 | 90.11 |
| Test article 2 | | 37 | 14.51 | 36.30 | 85.35 | 98.49 |
| Control | | 20 | −21.30 | −48.60 | −40.35 | −44.95 |
| 1 vs. 2 | t test p-values | | 0.0163 | 0.6767 | 0.2065 | 0.3936 |
| 1 vs. Control | | | 7.04E−16 | 5.27E−23 | 9.74E−11 | 5.69E−16 |
| 2 vs. Control | | | 1.06E−14 | 1.62E−24 | 1.10E−14 | 4.63E−17 |

Figure 3:
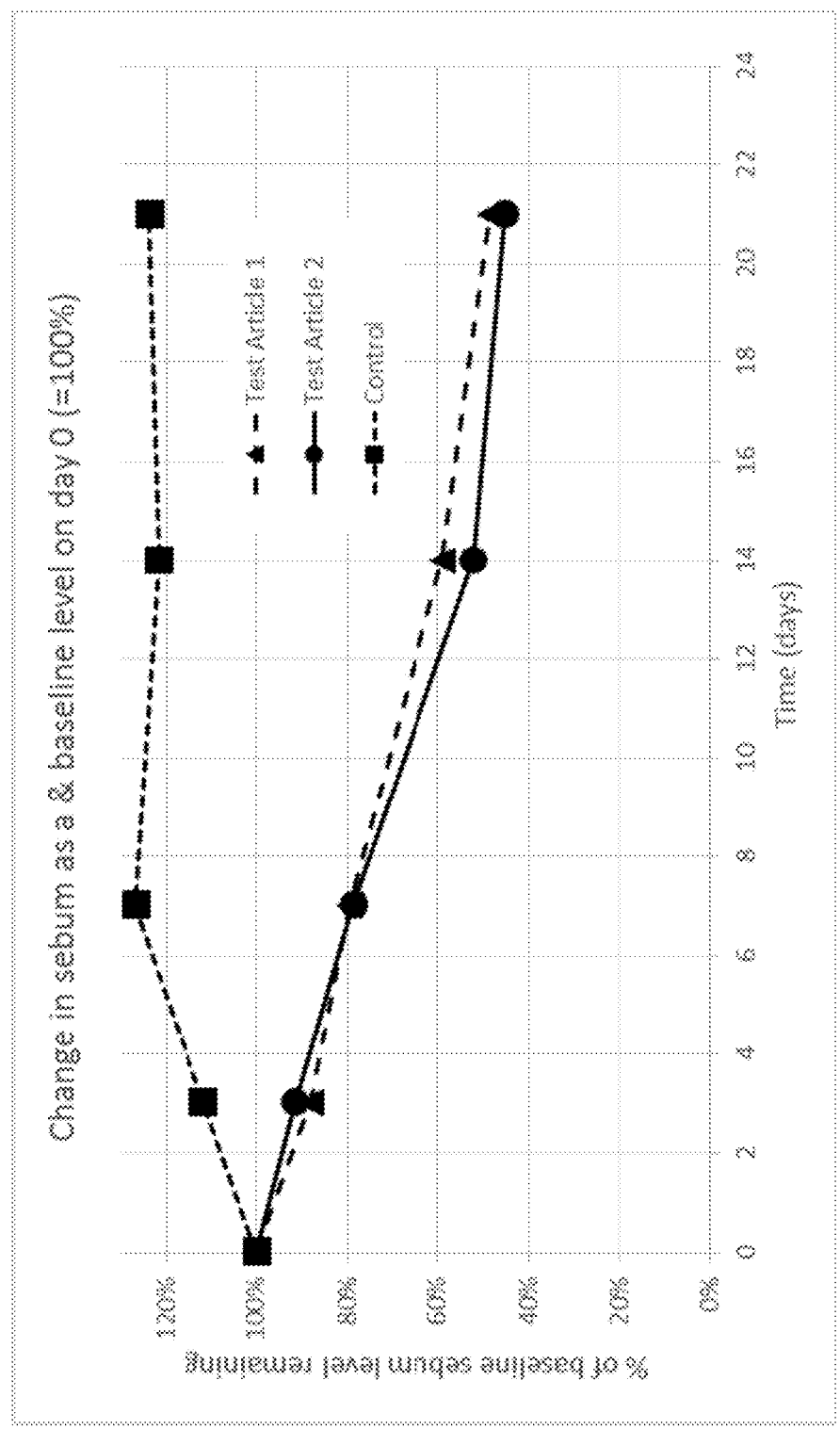
FIG. 3 is a graph illustrating the change in sebum levels over time after application of two compositions of the present invention comprising chlorhexidine digluconate to the skin of subjects, compared to a control composition.

As illustrated in FIG. 3, at all time points both test articles reduced sebum significantly more than the control at p<0.1%. On day 3 Test Article 1 was better than Test Article 2 at p<0.02. There was no significant difference in the effectiveness of the two test articles at all later time points.

By Day 21, both test articles had reduced the average sebum levels to less than 50% of the starting value.

2. Comedone Reduction

TABLE 3

Average reduction in occurrence of comedones from Day 0. A positive score indicates an increase in comedones.

|  | n | Day 3 | Day 7 | Day 14 | Day 21 |
|---|---|---|---|---|---|
| Test article 1 | 36 | −1.44 | −2.31 | −2.92 | −3.44 |
| Test article 2 | 37 | −1.14 | −1.97 | −2.84 | −3.38 |
| Control | 20 | 1.20 | 1.30 | 1.25 | 0.35 |
| 1 vs. 2 | t test p- | 0.414 | 0.468 | 0.903 | 0.934 |
| 1 vs. Control | values | 2.35E−06 | 2.98E−06 | 4.66E−05 | 6.63E−04 |
| 2 vs. Control |  | 1.08E−07 | 2.93E−05 | 7.20E−05 | 8.97E−05 |

Figure 4:
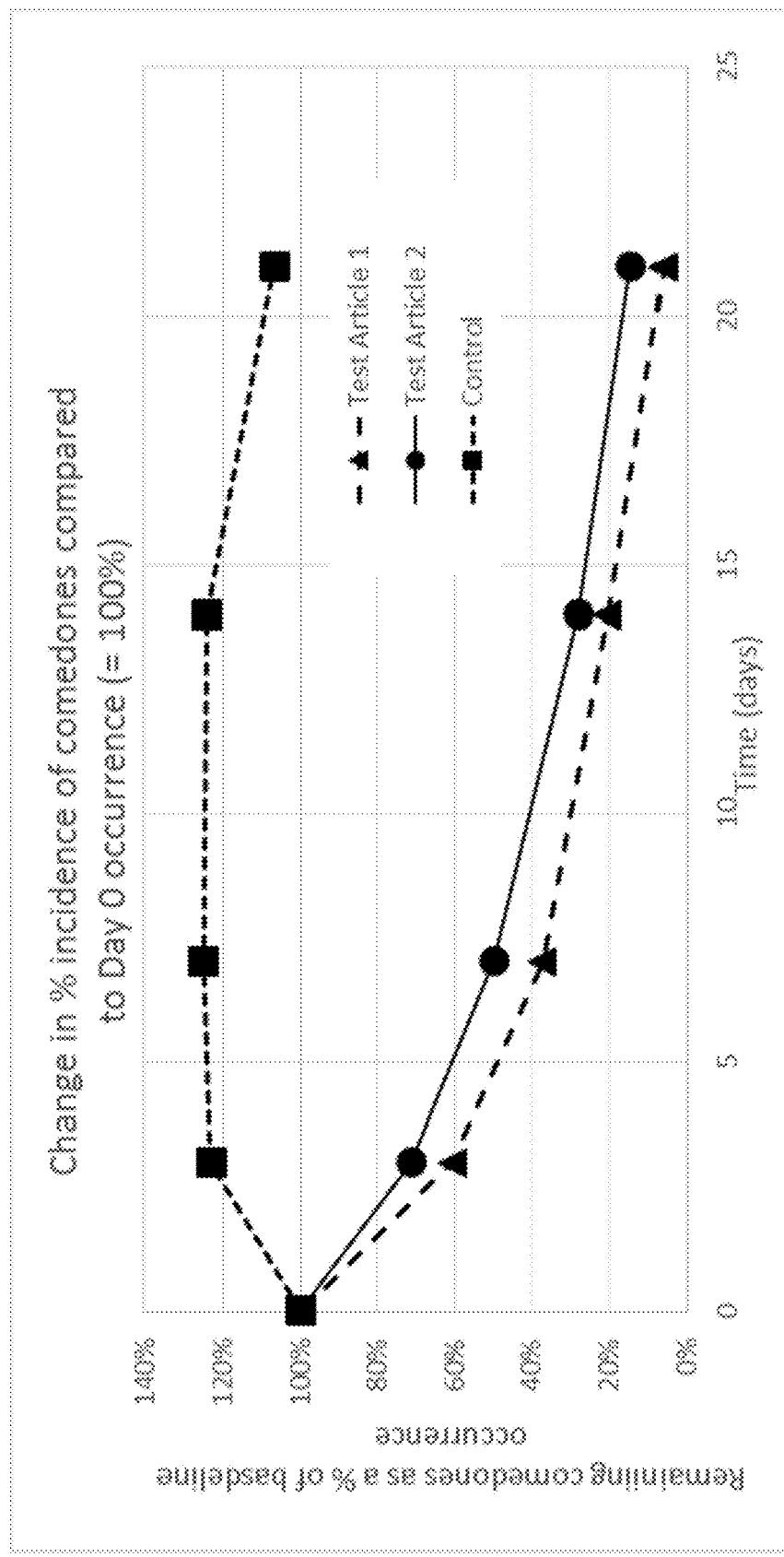
FIG. 4 is a graph illustrating the change in the number of comedones over time after application of two compositions of the present invention comprising chlorhexidine digluconate to the skin of subjects, compared to a control composition.

As illustrated in FIG. 4, at all time points both test articles reduced comedones significantly more than the control at p<0.1%. There was no significant difference in the effectiveness of the two test articles at all time points.

3. Papule Reduction

TABLE 4

Analysis of progression participants who had blemishes at day 0

|  | n | Day 0 | Day 3 | Day 7 | Day 14 | Day 21 |
|---|---|---|---|---|---|---|
| Test article 1 | 5 | 13 | 5 | 1 | 0 | 0 |
| Test article 2 | 7 | 16 | 9 | 5 | 0 | 0 |
| Control | 4 | 10 | 9 | 8 | 5 | 3 |

In those participants who began the trial with at least one papule, all treatments showed a reduction in papule numbers over 21 days.

TABLE 5

Probabilities of U-statistic (Mann-Whitney) calculated on lesion reductions from Day 0

|  | D3 v D0 | D7 vs D0 | D14 vs D0 | D21 vs D0 |
|---|---|---|---|---|
| 1 vs. 2 | 0.146 | 0.044 | 0.373 | 0.373 |
| 1 vs. Control | 0.043 | 0.019 | 0.056 | 0.089 |
| 2 vs. Control | 0.110 | 0.093 | 0.110 | 0.254 |

The test statistic (U) shows that Test article 1 was better than Control @<5% on Day 3 and Day 7 and @<10% on Day 14 and Day 21 and better that test article 2 @<5% on Day 7. Test article 2 was better than Control @<10% on Day 7

4. Pustule Reduction

TABLE 6

Reduction in pustule numbers from day 0. A positive score indicates an increase in numbers of pustules.

|  | n | Day 3 | Day 7 | Day 14 | Day 21 |
|---|---|---|---|---|---|
| Test article 1 | 36 | −1.28 | −1.97 | −2.11 | −2.17 |
| Test article 2 | 37 | −0.92 | −1.49 | −1.57 | −1.59 |
| Control | 20 | 0.60 | 0.05 | 0.15 | −0.75 |
| 1 vs. 2 | t test p- | 0.127 | 0.221 | 0.228 | 0.226 |
| 1 vs. Control | values | 2.71E−08 | 2.00E−05 | 9.67E−05 | 1.37E−02 |
| 2 vs. Control |  | 8.60E−07 | 7.48E−04 | 1.04E−03 | 9.15E−02 |

Figure 5:
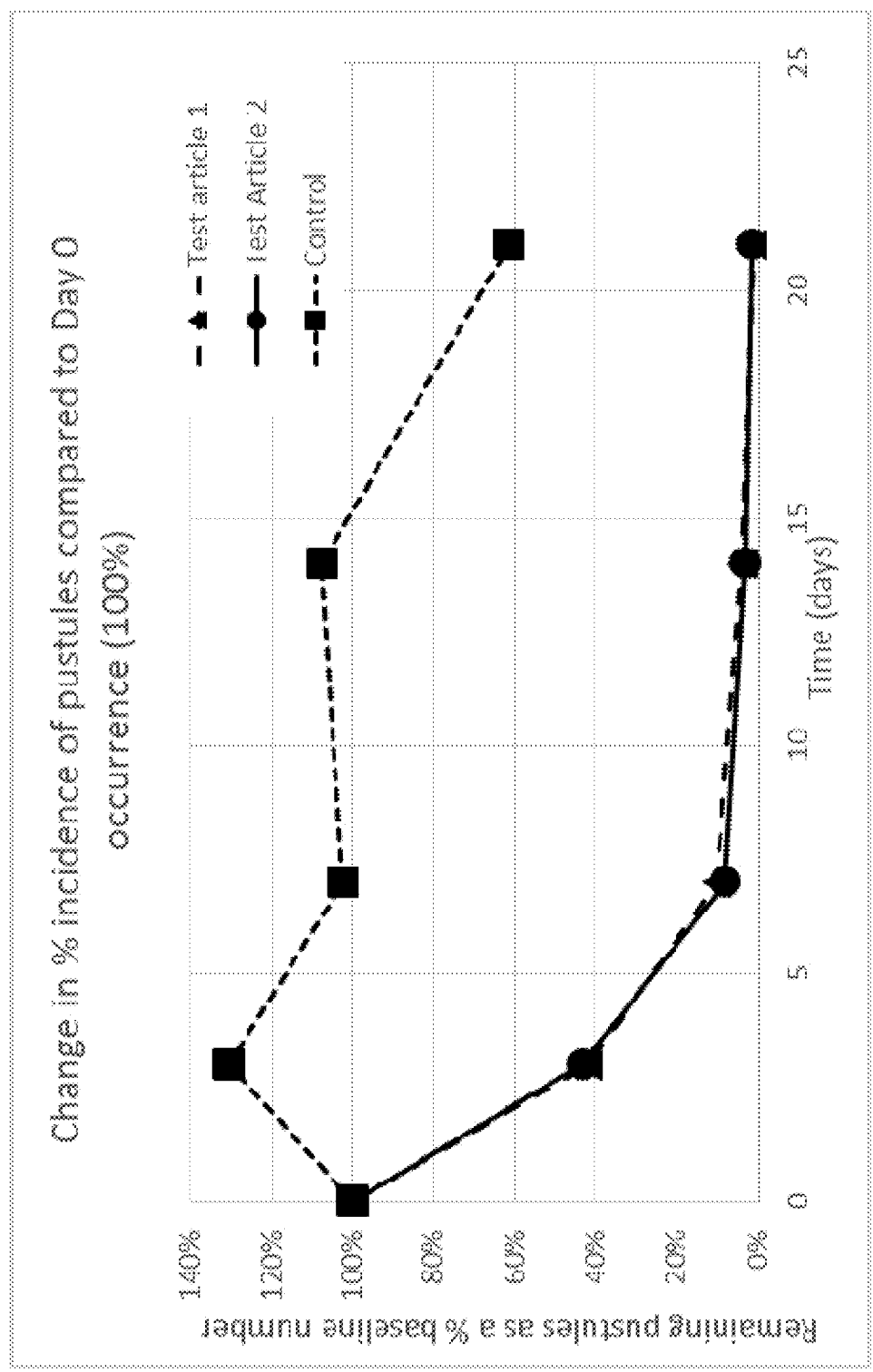
FIG. 5 is a graph illustrating the change in the number of pustules over time after application of two compositions of the present invention comprising chlorhexidine digluconate to the skin of subjects, compared to a control composition.

As illustrated in FIG. 5, at all time points from Day 3 to Day 14 both test articles reduced pustule numbers significantly more than the control at p<0.1%. At Day 21, test article 1 still outperformed control at p<2.0%; test article 2 outperformed control at p<10%. There was no significant difference in the effectiveness of the two test articles at all time points.

EXAMPLE 3: A STUDY IN VOLUNTEERS TO INVESTIGATE THE SENSATION PRODUCED USING THREE FORMULATIONS COMPRISING CAPSAICIN

Method

Three formulations comprising capsaicin at a concentration of 0.025% by weight were applied to the skin of three individuals. The first formulation ("TP1") comprised the insoluble aggregates of capsaicin in combination with Transfersomes™ comprising menthol. The second ("TP2") comprised insoluble and inflexible liposomes comprising capsaicin and menthol in combination with Transfersomes™ comprising menthol. The third formulation ("TP3") comprised the insoluble aggregates of capsaicin in combination with empty, fragrance-free Sequessomes™

The three starting materials used to formulate TP1, TP2 and TP3 are set out below.

TP1 (PD-14-0072) was formed by taking 100 g of Start Material 1, and adding/mixing in 0.25 g of a 100 mg/g capsaicin solution in ethanol.

TP2 (PD-14-0073) was formed by taking 90 g of Start Material 1 and adding/mixing in 10 g of Start Material 2.

TP3 (PD-14-0074) was formed by taking 100 g of Start Material 3, and adding/mixing in 0.25 g of a 100 mg/g capsaicin solution in ethanol.

Start Materials

Start Material 1 (Flexible, Menthol-Fragranced Vesicles):

|  | Quantity Required Per 100 g Final Product (g) |
|---|---|
| Organic Phase - Empty Transfersome Intermediate | |
| SPC (Dry Mass) | 6.87000 |
| Ethanol | 3.65100 |
| BHT | 0.02000 |
| Methyl-4-hydroxybenzoate | 0.25000 |
| Ethyl-4-hydroxybenzoate | 0.25000 |
| Benzyl alcohol | 0.52500 |
| Polysorbate 80 | 0.85000 |
| Capsaicin | 0.00000 |
| Menthol | 0.10000 |
| Organic Phase Sub-Total | 12.51600 |
| Aqueous Phase - Empty Transfersome Intermediate | |
| Sodium dihydrogen orthophosphate 2 $H_2O$ | 0.03700 |
| disodium hydrogen orthophosphate 12 $H_2O$ | 0.45300 |
| Sodium EDTA | 0.10000 |
| Water | 45.22700 |
| Aqueous Phase Sub-Total | 45.81700 |
| Transfersome Intermediate Total | 58.33300 |
| Gel Phase - Final Product | |
| Sodium dihydrogen orthophosphate 2 $H_2O$ | 0.02400 |
| disodium hydrogen orthophosphate 12 $H_2O$ | 0.30200 |
| Sodium hydroxide | 0.63000 |
| Carbopol 974P NF | 1.25000 |
| Glycerol | 3.00000 |
| Water | 36.46100 |
| Gel Phase Sub-Total | 41.66700 |
| Overall Total | 100.00000 |

Start Material 2 (Capsaisin Liposomes):

|  | Quantity Required Per 100 g Final Product (g) |
|---|---|
| Organic Phase - Liposome Intermediate | |
| SPC (Dry Mass) | 6.87000 |
| Ethanol | 4.25100 |
| BHT | 0.02000 |
| Methyl-4-hydroxybenzoate | 0.25000 |
| Ethyl-4-hydroxybenzoate | 0.25000 |
| Benzyl alcohol | 0.52500 |
| Polysorbate 80 | 0.00000 |
| Capsaicin | 0.25000 |
| Menthol | 0.10000 |
| Organic Phase Sub-Total | 12.51600 |
| Aqueous Phase - Liposome Intermediate | |
| Sodium dihydrogen orthophosphate 2 $H_2O$ | 0.03700 |
| disodium hydrogen orthophosphate 12 $H_2O$ | 0.45300 |
| Sodium EDTA | 0.10000 |
| Water | 45.22700 |
| Aqueous Phase Sub-Total | 45.81700 |
| Liposome Intermediate Total | 58.33300 |
| Gel Phase - Final Product | |
| Sodium dihydrogen orthophosphate 2 $H_2O$ | 0.02400 |
| disodium hydrogen orthophosphate 12 $H_2O$ | 0.30200 |
| Sodium hydroxide | 0.63000 |
| Carbopol 974P NF | 1.25000 |
| Glycerol | 3.00000 |
| Water | 36.46100 |
| Gel Phase Sub-Total | 41.66700 |
| Overall Total | 100.00000 |

Start Material 3 (Flexible, Empty, Fragrance-Free Vesicles):

|  | Quantity Required Per 100 g Final Product (g) |
|---|---|
| Organic Phase - Sequessome Intermediate | |
| SPC (Dry Mass) | 6.87000 |
| Ethanol | 3.75100 |
| BHT | 0.02000 |
| Methyl-4-hydroxybenzoate | 0.25000 |
| Ethyl-4-hydroxybenzoate | 0.25000 |
| Benzyl alcohol | 0.52500 |
| Polysorbate 80 | 0.85000 |
| Capsaicin | 0.00000 |
| Menthol | 0.00000 |
| Organic Phase Sub-Total | 12.51600 |
| Aqueous Phase - Empty Sequessome Intermediate | |
| Sodium dihydrogen orthophosphate 2 $H_2O$ | 0.03700 |
| disodium hydrogen orthophosphate 12 $H_2O$ | 0.45300 |
| Sodium EDTA | 0.10000 |
| Water | 45.22700 |
| Aqueous Phase Sub-Total | 45.81700 |
| Sequessome Intermediate Total | 58.33300 |
| Gel Phase - Final Product | |
| Sodium dihydrogen orthophosphate 2 $H_2O$ | 0.02400 |
| disodium hydrogen orthophosphate 12 $H_2O$ | 0.30200 |
| Sodium hydroxide | 0.63000 |
| Carbopol 974P NF | 1.25000 |
| Glycerol | 3.00000 |
| Water | 36.46100 |
| Gel Phase Sub-Total | 41.66700 |
| Overall Total | 100.00000 |

Summary Formulae:

| Title Ingredient | Start Material 1 | Start Material 2 | Start Material 3 | PD-14-0072 (Start Material 1 plus 0.025% capsaicin in ethanol) | PD-14-0073 (90% Start Material 1 plus 10% Start Material 2) | PD-14-0074 (Start Material 3 plus 0.025% capsaicin in ethanol) |
|---|---|---|---|---|---|---|
| SPC (dry mass) | 6.870 g | 6.870 g | 6.870 g | 6.870 g | 6.870 g | 6.870 g |
| Polysorbate 80 | 0.850 g | — | 0.850 g | 0.850 g | 0.765 g | 0.850 g |
| Benzylalcohol | 0.525 g | 0.525 g | 0.525 g | 0.525 g | 0.525 g | 0.525 g |
| Methyl-4-hydroxybenzoate | 0.250 g | 0.250 g | 0.250 g | 0.250 g | 0.250 g | 0.250 g |
| Ethyl-4-hydroxybenzoate | 0.250 g | 0.250 g | 0.250 g | 0.250 g | 0.250 g | 0.250 g |
| Butylhydroxytoluene | 0.020 g | 0.020 g | 0.020 g | 0.020 g | 0.020 g | 0.020 g |
| Disodium EDTA | 0.100 g | 0.100 g | 0.100 g | 0.100 g | 0.100 g | 0.100 g |
| Disodium hydrogen phosphate 12 $H_2O$ | 0.755 g | 0.755 g | 0.755 g | 0.755 g | 0.755 g | 0.755 g |
| Sodium dihydrogen phosphate 2 $H_2O$ | 0.061 g | 0.061 g | 0.061 g | 0.061 g | 0.061 g | 0.061 g |
| Glycerol | 3.000 g | 3.000 g | 3.000 g | 3.000 g | 3.000 g | 3.000 g |
| Ethanol | 3.651 g | 4.251 g | 3.751 g | 3.876 g | 3.711 g | 3.976 g |
| Sodium hydroxide | 0.630 g | 0.630 g | 0.630 g | 0.630 g | 0.630 g | 0.630 g |
| Carbopol 974P NF | 1.250 g | 1.250 g | 1.250 g | 1.250 g | 1.250 g | 1.250 g |
| Water | 81.688 g | 81.688 g | 81.688 g | 81.688 g | 81.688 g | 81.688 g |
| Agent of Interest in continuous phase | | | | | | |
| Capsaicin | — | 0.250 g | — | 0.025 g | 0.025 g | 0.025 g |
| Agent of Interest in Transfersomes | | | | | | |
| Menthol | 0.100 g | 0.100 g | — | 0.100 g | 0.100 g | |
| Total mass | 100.000 g | 100.000 g | 100.000 g | 100.250 g | 100.000 g | 100.250 g |

Results

Following the application of the formulations to the skin of three individuals, the following combined results were recorded regarding the onset, duration and intensity of the warming sensation produced by the capsaicin.

TABLE 8

Combined results of three individuals testing "TP1", "TP2" and "TP3"

| Product code | TP1 (PD-14-0072) | TP2 (PD-14-0073) | TP3 (PD-14-0074) |
|---|---|---|---|
| Capsaicin | Insoluble aggregate | In liposomes | Insoluble aggregate |
| Menthol | In membranes of Transfersomes ™ | In membranes of Transfersomes ™ and of liposomes | None |
| Sequessomes | No | No | Yes |
| Test product | TP1 | TP2 | TP3 |
| Onset of sensation | 5 to 30 mins | 5 to 30 mins | 15-30 mins |
| Onset of optimal sensation | 15 to 60 mins | 15 to 60 mins | 30-60 mins |
| Duration of sensation (capsaicin) | 60 to 120 mins | 45 to 180 mins | 45 to 60 mins |
| Intensity (capsaicin) | Pleasant | Pleasant | Pleasant |

EXAMPLE 4: EXEMPLARY COMPOSITIONS COMPRISING (I) GLUCOSAMINE HYDROCHLORIDE AND CHONDROITIN SULPHATE (CBL-LS-15-002) AND (II) N-ACETYL GLUCOSAMINE SULPHATE AND CHONDROITIN SULPHATE (CBL-LS-15-003)

Below is provided two exemplary formulations of chondroitin and glucosamine. The first (CBL-LS-15-002) comprises glucosamine hydrochloride and chondroitin sulphate as the "free" AOIs in the continuous phase and palmitoyl ascorbate and tocopheryl lineoleate tethered to Tethersomes. The second (CBL-LS-15-00) comprises N-acetyl glucosamine sulphate and chondroitin sulphate as the "free" AOIs in the continuous phase and palmitoyl ascorbate and tocopheryl lineoleate tethered to Tethersomes.

| Ingredient | CBL-LS-15-002 Supplement Gel | CBL-LS-15-003 Supplement Gel |
|---|---|---|
| SPC (dry mass) | 6.870 g | 6.870 g |
| Polysorbate 80 | 0.850 g | 0.850 g |
| Benzylalcohol | 0.525 g | 0.525 g |
| Methyl-4-hydroxybenzoate | 0.250 g | 0.250 g |
| Ethyl-4-hydroxybenzoate | 0.250 g | 0.250 g |
| Butylhydroxyanisole | 0.020 g | 0.020 g |
| Linalool | 0.100 g | 0.100 g |
| Sodium metabisulphite | 0.050 g | 0.050 g |
| Disodium EDTA | 0.100 g | 0.100 g |
| Disodium hydrogen phosphate 12 $H_2O$ | 0.530 g | 0.530 g |
| Citric acid monohydrate | 0.128 g | 0.128 |
| Glycerol | 3.000 g | 3.000 g |
| Ethanol | 3.455 g | 3.455 g |
| Sodium hydroxide | 0.160 g | 0.160 g |
| Carbopol 974P NF | 0.750 g | 0.750 g |
| Water | 82.366 g | 82.366 g |
| Agents of Interest in Continuous Phase | | |
| Chondroitin Sulphate | 0.200 g | 0.200 g |
| Glucosamine •HCl | 0.200 g | |
| N-Acetyl glucosamine sulphate | | 0.200 g |
| Agents of Interest - Tethered to Tethersomes | | |
| Palmitoyl ascorbate | 0.096 g | 0.096 g |
| Tocopheryl linoleate | 0.100 g | 0.100 g |

EXAMPLE 5: A USER TRIAL STUDY IN HEALTHY VOLUNTEERS TO INVESTIGATE THE EFFICACY OF A TEST ARTICLE COMPRISING CAFFEINE IN IMPROVING THE APPEARANCE OF PERIORBITAL SKIN

This study tested the efficacy of a formulation comprising caffeine and tocopherol in the continuous phase and three types of deformable colloidal particles: 1) Tethersomes to which palmitoyl ascorbate is tethered, 2) Tethersomes to which palmitoyl tripeptide-1 is tethered, and 3) Tethersomes to which palmitoyl tetrapeptide-7 is tethered.

Methods
Summary Protocol

| | |
|---|---|
| Study design: | Single-blind |
| Test article: | CBL-DERM-15-013 Periorbital skin serum |
| Duration of treatment: | 4 weeks |
| Number of subjects: | 102 |
| Type of subjects: | Healthy male and female subjects (from a breadth of ethnicities) aged between 40 and 70 years old (in equal proportions, 33% each 10 year age group), from a breadth of ethnicities and with a variety of skin types (normal, combination, dry, oily, sensitive) who suffer from the appearance of two of the following characteristics: Periorbital puffiness - swelling around the eyes Puffiness below the lower eyelids - 'eye bags' Periorbital dark circles caused by a) aging b) heredity and c) hyperpigmentation (dark skinned people) (There must be an equal representation of all three characteristics to ensure claims objectivity). All subjects must have visible wrinkles, fine lines and crow's feet around the eye area |
| Observations: | Subjects were asked to apply the product as per usage instructions. They were then asked to complete a Self-Perception Questionnaire (SPQ) after two weeks and at the end of the study after four weeks. |
| Treatment: | Subjects were issued with samples of the test article and directions for use following standard in-use application regime. |
| Location | Princeton Consumer Research Harbour House 23 Chandlers Quay Maldon CM9 4LF United Kingdom |

Summary Formula for CBL-DERM-15-013:

| Ingredient | CBL-DERM-15-013 Periorbital Skin |
|---|---|
| SPC (dry mass) | 6.870 g |
| Polysorbate 80 | 0.714 g |
| Benzylalcohol | 0.525 g |
| Methyl-4-hydroxybenzoate | 0.250 g |
| Ethyl-4-hydroxybenzoate | 0.250 g |
| Butylhydroxyanisole | 0.020 g |
| Linalool | 0.100 g |
| Sodium metabisulphite | 0.050 g |
| Disodium EDTA | 0.100 g |
| Disodium hydrogen phosphate 12 $H_2O$ | 0.530 g |
| Citric acid monohydrate | 0.128 g |
| Glycerol | 3.000 g |
| Ethanol | 3.479 g |
| Sodium hydroxide | 0.160 g |
| Carbopol 974P NF | 0.750 g |
| Water | 82.716 g |
| Agent of Interest in Continuous Phase | |
| Caffeine | 0.050 g |
| Tocopherol | 0.200 g |
| Agents of Interest - tethered to Tethersomes | |
| Palmitoyl tripeptide-1 | 0.006 g |
| Palmitoyl tetrapeptide-7 | 0.006 g |
| Palmitoyl ascorbate | 0.096 g |

Detailed Formulation Information for CBL-DERM-15-013:

| | Quantity Required Per 100 g Final Product (g) |
|---|---|
| Organic Phase - 1600 ppm PAA Intermediate | |
| Soy phosphatidylcholine (SPC) | 4.12200 |
| Ethanol | 1.99660 |
| Butylhydroxyanisole (BHA) | 0.01200 |
| Methyl-4-hydroxybenzoate | 0.15000 |
| Ethyl-4-hydroxybenzoate | 0.15000 |
| Benzyl alcohol | 0.31500 |
| Polysorbate 80 | 0.40800 |
| Palmitoyl ascorbic acid | 0.09600 |
| +/− alpha tocopherol | 0.20000 |
| Linalool | 0.06000 |
| Organic Phase Sub-Total | 7.50960 |
| Aqueous Phase - 1600 ppm PAA intermediate | |
| Sodium metabisulphite | 0.03000 |
| Citric acid monohydrate | 0.04320 |
| Disodium EDTA | 0.06000 |
| Disodium hydrogen orthophosphate dodecahydrate | 0.17280 |
| Caffeine | 0.05000 |
| Water | 27.13420 |
| Aqueous Phase Sub-Total | 27.49020 |
| PAA Tethersome Intermediate Total | 34.99980 |
| Organic Phase - 300 ppm Tetrapeptide Intermediate | |
| Soy phosphatidylcholine (SPC) | 1.37400 |
| Ethanol | 0.74120 |
| Butylhydroxyanisole (BHA) | 0.00400 |
| Methyl-4-hydroxybenzoate | 0.05000 |
| Ethyl-4-hydroxybenzoate | 0.05000 |

-continued

| | Quantity Required Per 100 g Final Product (g) |
|---|---|
| Benzyl alcohol | 0.10500 |
| Polysorbate 80 | 0.15300 |
| Palmitoyl peptide | 0.00600 |
| Linalool | 0.02000 |
| Organic Phase Sub-Total | 2.50320 |
| Aqueous Phase - 300 ppm Tetrapeptide Intermediate | |
| Sodium metabisulphite | 0.01000 |
| Citric acid monohydrate | 0.01440 |
| Disodium EDTA | 0.02000 |
| Disodium hydrogen orthophosphate dodecahydrate | 0.05760 |
| Water | 9.06140 |
| Aqueous Phase Sub-Total | 9.16340 |
| Tetrapeptide Tethersome Intermediate Total | 11.66660 |
| Organic Phase - 300 ppm Tripeptide Intermediate | |
| Soy phosphatidylcholine (SPC) | 1.37400 |
| Ethanol | 0.74120 |
| Butylhydroxyanisole (BHA) | 0.00400 |
| Methyl-4-hydroxybenzoate | 0.05000 |
| Ethyl-4-hydroxybenzoate | 0.05000 |
| Benzyl alcohol | 0.10500 |
| Polysorbate 80 | 0.15300 |
| Palmitoyl peptide | 0.00600 |
| Linalool | 0.02000 |
| Organic Phase Sub-Total | 2.50320 |
| Aqueous Phase - 300 ppm Tripeptide Intermediate | |
| Sodium metabisulphite | 0.01000 |
| Citric acid monohydrate | 0.01440 |
| Disodium EDTA | 0.02000 |
| Disodium hydrogen orthophosphate dodecahydrate | 0.05760 |
| Water | 9.06140 |
| Aqueous Phase Sub-Total | 9.16340 |
| Tripeptide Tethersome Intermediate Total | 11.66660 |
| Sum of Tethersome Intermediates | 58.33300 |
| Gel Phase - Final Product | |
| Sodium hydroxide | 0.16000 |
| Carbopol 974P NF | 0.75000 |
| Glycerol | 3.00000 |
| Citric acid monohydrate | 0.05600 |
| Disodium hydrogen orthophosphate dodecahydrate | 0.24200 |
| Water | 37.45900 |
| Gel Phase Sub-Total | 41.66700 |
| Overall Total | 100.00000 |

Results

Within-treatment analysis ($p<0.05$) of periorbital clinical assessment shows there to be a statistically significant reduction in wrinkles (15.69%), fine lines (31.22%), crow's feet (21.47%), puffiness (38.07%), dark circles (26.01%) and eye bags (38.94%) after 4 weeks of product usage.

The product performed statistically favourably over the 4 week study in the majority of attributes under Clearcast guidelines of advertising. The product showed a preference or favourability in the majority of attributes:

After using the product, 96.08% of users agreed, or strongly agreed the product reduced the appearance of puffiness and swelling around my eyes.

After using the product, 96.08% of users agreed, or strongly agreed their skin felt and looked less thin.

After using the product, 93.14% of users agreed, or strongly agreed their skin felt more elastic.

After using the product, 96.08% of users agreed, or strongly agreed the product reduced the appearance of swelling and puffiness below the lower eyelids (eye bags).

After using the product, 90.20% of users agreed, or strongly agreed the product lifted sagged skin (reduction in skin droopiness and sagging).

After using the product, 92.16% of users agreed, or strongly agreed the product reduced the appearance of under eye dark circles.

After using the product, 95.10% of users agreed, or strongly agreed their skin looked and felt more firm.

After using the product, 90.20% of users agreed, or strongly agreed there was a reduction in fine lines (inc. crow's feet) around the eye area.

After using the product, 87.25% of users agreed, or strongly agreed there was a reduction in deep wrinkles (inc. crow's feet) around the eye area.

After using the product, 93.14% of users agreed, or strongly agreed their skin tone looked more even.

After using the product, 90.20% of users agreed, or strongly agreed their eye contour looked and felt tighter.

After using the product, 90.20% of users agreed, or strongly agreed their eye contour looked more toned/lifted.

After using the product, 96.08% of users agreed, or strongly agreed their eyes looked rested/less tired.

After using the product, 97.06% of users agreed, or strongly agreed their eye skin was more hydrated.

After using the product, 95.10% of users agreed, or strongly agreed their skin looked smoother.

After using the product, 99.02% of users agreed, or strongly agreed the product was gentle and well tolerated.

After using the product, 75.49% of users stated, yes, they would buy this product instead of their usual product.

After using the product, 86.27% of users stated, yes, they would recommend this product to a friend.

After using the product, 46.08% of users stated, they looked at least 5 years younger.

EXAMPLE 6: A USER TRIAL STUDY IN HEALTHY VOLUNTEERS TO INVESTIGATE THE EFFICACY OF A TEST ARTICLE COMPRISING TOCOPHEROL AND TRIDECYL SALICYLATE IN IMPROVING SKIN TONE

This study tested the efficacy of a formulation comprising a racemic mixture of alpha tocopherol in the continuous phase and two types of colloidal particles: 1) Tethersomes to which tridecyl salicylate is tethered and 2) Tethersomes to which palmitoyl ascorbate and tocopheryl linoleate are tethered.

Methods
Summary Protocol

| | |
|---|---|
| Study design: | Single-blind |
| Test article: | CBL-DERM-15-014 Skin tone serum |
| Duration of treatment: | 4 weeks |
| Number of subjects: | 110 |
| Type of subjects: | Healthy male (20%) and female (80%) participants aged between 20 and 70 years (equal proportions of each 10 year age group; 20's, 30's, 40's, 50's, 60's, 70's), from a Breadth of Ethnicities and with a Variety of Skin Types. Subjects suffer from one well pronounced or two out of the following six conditions; Melasma or Chloasma spots, Uneven skin tone, Age, sun or "liver" spots, Freckles, Post-inflammatory hyperpigmentation or Periorbital hyperpigmentation (dark circles). |
| Observations: | Subjects were asked to apply the product as per usage instructions. They were asked to complete a Self-Perception Questionnaire (SPQ) at the end of Weeks 3 and 6. |
| Treatment: | Subjects were issued with samples of each test article and directions for use following standard in-use application regime. |
| Location | Princeton Consumer Research Harbour House 23 Chandlers Quay Maldon CM9 4LF United Kingdom |

Summary Formula for CBL-DERM-15-014:

| Ingredient | CBL-DERM-15-014 Uneven Skin Tone |
|---|---|
| SPC (dry mass) | 6.870 g |
| Polysorbate 80 | 0.850 g |
| Benzylalcohol | 0.525 g |
| Methyl-4-hydroxybenzoate | 0.250 g |
| Ethyl-4-hydroxybenzoate | 0.250 g |
| Butylhydroxyanisole | 0.020 g |
| Linalool | 0.100 g |
| Sodium metabisulphite | 0.050 g |
| Disodium EDTA | 0.100 g |
| Disodium hydrogen phosphate 12 $H_2O$ | 0.530 g |
| Citric acid monohydrate | 0.128 g |
| Glycerol | 3.000 g |
| Ethanol | 3.255 g |
| Sodium hydroxide | 0.160 g |
| Carbopol 974P NF | 0.750 g |
| Water | 82.766 g |
| Agent of Interest in Continuous Phase | |
| Tocopherol | 0.100 g |
| Agents of Interest - tethered to Tethersomes | |
| Palmitoyl ascorbate | 0.096 g |
| Tocopheryl Linoleate | 0.100 g |
| Tridecyl Salicylate | 0.100 g |
| pH* | 5.5 |

*Final pH approximate; to be confirmed
**The source of SC dry mass for Uneven Skin Tone will be lipoid Phospholipon 90K (P90K). The quantity of P90K and ethanol to be added should be calculated accordingly.

Detailed Formulation Information for CBL-DERM-15-014:

| | Quantity Required Per 100 g Final Product (g) |
|---|---|
| Organic Phase - Tridecyl Salicylate Intermediate | |
| Soy phosphatidylcholine (SPC) | 3.43500 |
| Ethanol | 1.67550 |
| Butylhydroxyanisole (BHA) | 0.01000 |
| Methyl-4-hydroxybenzoate | 0.12500 |
| Ethyl-4-hydroxybenzoate | 0.12500 |
| Benzyl alcohol | 0.26250 |
| Polysorbate 80 | 0.42500 |
| Tridecyl Salicylate | 0.10000 |
| +/− alpha tocopherol | 0.05000 |
| Linalool | 0.05000 |
| Organic Phase Sub-Total | 6.25800 |
| Aqueous Phase - Tridecyl Salicylate Intermediate | |
| Citric acid monohydrate | 0.03600 |
| Disodium EDTA | 0.05000 |
| Sodium metabisulphite | 0.02500 |
| Disodium hydrogen orthophosphate dodecahydrate | 0.14400 |
| Water | 22.65350 |
| Aqueous Phase Sub-Total | 22.90850 |
| Tridecyl Salicylate Tethersome Intermediate Total | 29.16650 |
| Organic Phase - PAA/Tocopheryl Linoleate Intermediate | |
| Soy phosphatidylcholine (SPC) | 3.43500 |
| Ethanol | 1.57950 |
| Butylhydroxyanisole (BHA) | 0.01000 |
| Methyl-4-hydroxybenzoate | 0.12500 |
| Ethyl-4-hydroxybenzoate | 0.12500 |
| Benzyl alcohol | 0.26250 |
| Polysorbate 80 | 0.42500 |

-continued

| | Quantity Required Per 100 g Final Product (g) |
|---|---|
| Palmitoyl ascorbic acid | 0.09600 |
| Tocopheryl linoleate | 0.10000 |
| +/− alpha tocopherol | 0.05000 |
| Linalool | 0.05000 |
| Organic Phase Sub-Total | 6.25800 |
| Aqueous Phase - PAA/Tocopheryl Linoleate Intermediate | |
| Citric acid monohydrate | 0.03600 |
| Disodium EDTA | 0.05000 |
| Sodium metabisulphite | 0.02500 |
| Disodium hydrogen orthophosphate dodecahydrate | 0.14400 |
| Water | 22.65350 |
| Aqueous Phase Sub-Total | 22.90850 |
| PAA/Tocopheryl Linoleate Tethersome Intermediate Total | 29.16650 |
| Sum of Tethersome Intermediates | 58.33300 |
| Gel Phase - Final Product | |
| Sodium hydroxide | 0.16000 |
| Carbopol 974P NF | 0.75000 |
| Glycerol | 3.00000 |
| Citric acid monohydrate | 0.05600 |
| Disodium hydrogen orthophosphate dodecahydrate | 0.24200 |
| Water | 37.45900 |
| Gel Phase Sub-Total | 41.66700 |
| Overall Total | 100.00000 |

Results

The product did perform statistically favourably over the 6 week study in the majority of attributes under Clearcast guidelines of advertising. The product did show a preference or favourability in the majority of attributes:

After using the product, 100% of users agreed, or strongly agreed the product reduced the appearance of fine lines and wrinkles.

After using the product, 100% of users agreed, or strongly agreed their skin looked significantly smoother.

After using the product, 100% of users agreed, or strongly agreed their skin felt significantly more healthy.

After using the product, 96.36% of users agreed, or strongly agreed their skin felt more elastic After using the product, 99.09% of users agreed, or strongly agreed their complexion looks younger.

After using the product, 99.09% of users agreed, or strongly agreed their complexion is visibly improved.

After using the product, 100% of users agreed, or strongly agreed their complexion was visibly more radiant.

After using the product, 100% of users agreed, or strongly agreed their complexion looked significantly healthier.

After using the product, 98.18% of users agreed, or strongly agreed their skin toned looked significantly more even After using the product, 96.36% of users agreed, or strongly agreed that the amount of hyperpigmentation/pigmented skin blemishes were significantly reduced.

After using the product, 97.27% of users agreed, or strongly agreed that the size of hyperpigmentation/pigmented skin blemishes were significantly reduced.

After using the product, 99.09% of users agreed, or strongly agreed that hyperpigmentation/pigmented skin blemishes were significantly lighter.

After using the product, 20.00% of users agreed, or strongly agreed that hyperpigmented/pigmented skin blemishes totally disappeared.

After using the product, 100% of users agreed, or strongly agreed their periorbital dark circles got significantly lighter.

After using the product, 95.45% of users agreed, or strongly agreed this was the most effective hyperpigmentation solution they had used.

After using the product, 92.73% of users stated, yes, they would buy this product instead of their usual product.

After using the product, 100% of users stated, yes, they would recommend this product to a friend.

With reference to packaging/promotional claims, any results with a top 3 & 4 scoring greater than 80% are highly favourable.

The invention claimed is:

1. A composition comprising a colloidal dispersion and an Agent of Interest ("AOI"), wherein said colloidal dispersion comprises deformable colloidal particles comprising a surfactant and a phospholipid and wherein the AOI is not associated with the deformable colloidal particles, wherein the AOI comprises a biologically active agent, wherein the AOI comprises capsaicin.

2. The composition of claim 1 wherein the deformable colloidal particles comprise vesicles.

3. The composition of claim 1, wherein the capsaicin is present in the composition in the form of aggregates or wherein the capsaicin is associated with liposomes comprising one or more phospholipids.

4. The composition of claim 1, wherein the deformable colloidal particles comprise menthol in their membranes.

5. The composition of claim 1 wherein the phospholipid is selected from the group consisting of sphingomyelin, sphingomyelin lauroyl, phosphatidyl choline and phosphatidyl glycerol.

6. The composition of claim 1 wherein the surfactant is a non-ionic surfactant, optionally wherein the surfactant is polyoxyethylene (20) sorbitan monooleate (Polysorbate 80) or 2-[(Z)-octadec-9-enoxy]ethanol.

7. The composition of claim 1 wherein the composition comprises a phospholipid and a surfactant in a molar ratio of 1:30 to 30:1.

8. A kit comprising a container comprising the composition of claim 1 and instructions for administration of the composition to a patient in need thereof, wherein the composition is contained within a single compartment of said container.

* * * * *